United States Patent
Granland et al.

(10) Patent No.: US 12,029,767 B2
(45) Date of Patent: Jul. 9, 2024

(54) TREATING OR PREVENTING RESPIRATORY INFECTION

(71) Applicant: Telethon Kids Institute, Nedlands (AU)

(72) Inventors: Caitlyn Granland, Nedlands (AU); Lea-Ann Kirkham, Nedlands (AU); Peter Richmond, Nedlands (AU)

(73) Assignee: Telethon Kids Institute, Nedlands (AU)

( * ) Notice: Subject to any disclaimer, the term of this patent is extended or adjusted under 35 U.S.C. 154(b) by 267 days.

(21) Appl. No.: 17/337,052

(22) Filed: Jun. 2, 2021

(65) Prior Publication Data
US 2021/0369791 A1 Dec. 2, 2021

Related U.S. Application Data

(60) Provisional application No. 63/033,442, filed on Jun. 2, 2020.

(51) Int. Cl.
*A61K 35/74* (2015.01)
*A61K 9/00* (2006.01)
*A61P 31/04* (2006.01)
*A61P 31/12* (2006.01)

(52) U.S. Cl.
CPC ............ *A61K 35/74* (2013.01); *A61P 31/04* (2018.01); *A61P 31/12* (2018.01); *A61K 9/0043* (2013.01)

(58) Field of Classification Search
CPC ........... A61P 31/04; A61P 31/12; A61K 35/74
See application file for complete search history.

(56) References Cited

U.S. PATENT DOCUMENTS

2011/0206765 A1* 8/2011 Dunkley ................ A61P 31/04
424/490

OTHER PUBLICATIONS

Aguilera et al. "Inflammation as a Modulator of Host Susceptibility to Pulmonary Influenza, Pneumococcal, and Co-Infections", Feb. 11, 2020, Frontiers in Immunology, vol. 11, Article 105, p. 1-9. (Year: 2020).*
Atto et al. "In Vitro Anti-NTHi Activity of Haemophilin-Producing Strains of Haemophilus haemolyticus", Mar. 25, 2020, Pathogens, vol. 9, Article 243, p. 1-12. (Year: 2020).*
Christensen et al., "Classification of genera of Pasteurellaceae using conserved predicted protein sequences", J. Syst. Evol. Microbiol., vol. 68, 2018, pp. 2692-2696. (Year: 2018).*
Granland et al. "Nasal Delivery of a Commensal Pasteurellaceae Species Inhibits Nontypeable Haemophilus influenzae Colonization and Delays Onset of Otitis Media in Mice", Jan. 12, 2020, Infection and Immunity, vol. 88 Issue 4 Article e00685-19, p. 1-13. (Year: 2020).*
Kyd et al. "Killed whole bacterial cells, a mucosal delivery system for the induction of immunity in the respiratory tract and middle ear: an overview", 1999, Vaccine, vol. 17, p. 1775-1781. (Year: 1999).*

(Continued)

*Primary Examiner* — Gary B Nickol
*Assistant Examiner* — Amelia Nicole Dickens
(74) *Attorney, Agent, or Firm* — Michael Best & Friedrich LLP

(57) ABSTRACT

The present disclosure relates to a method for treating or preventing a viral and/or bacterial respiratory infection in a subject, the method comprising administering to the respiratory tract of the subject an effective amount of one or more bacteria from family Pasteurellaceae.

19 Claims, 11 Drawing Sheets

Figure 1:
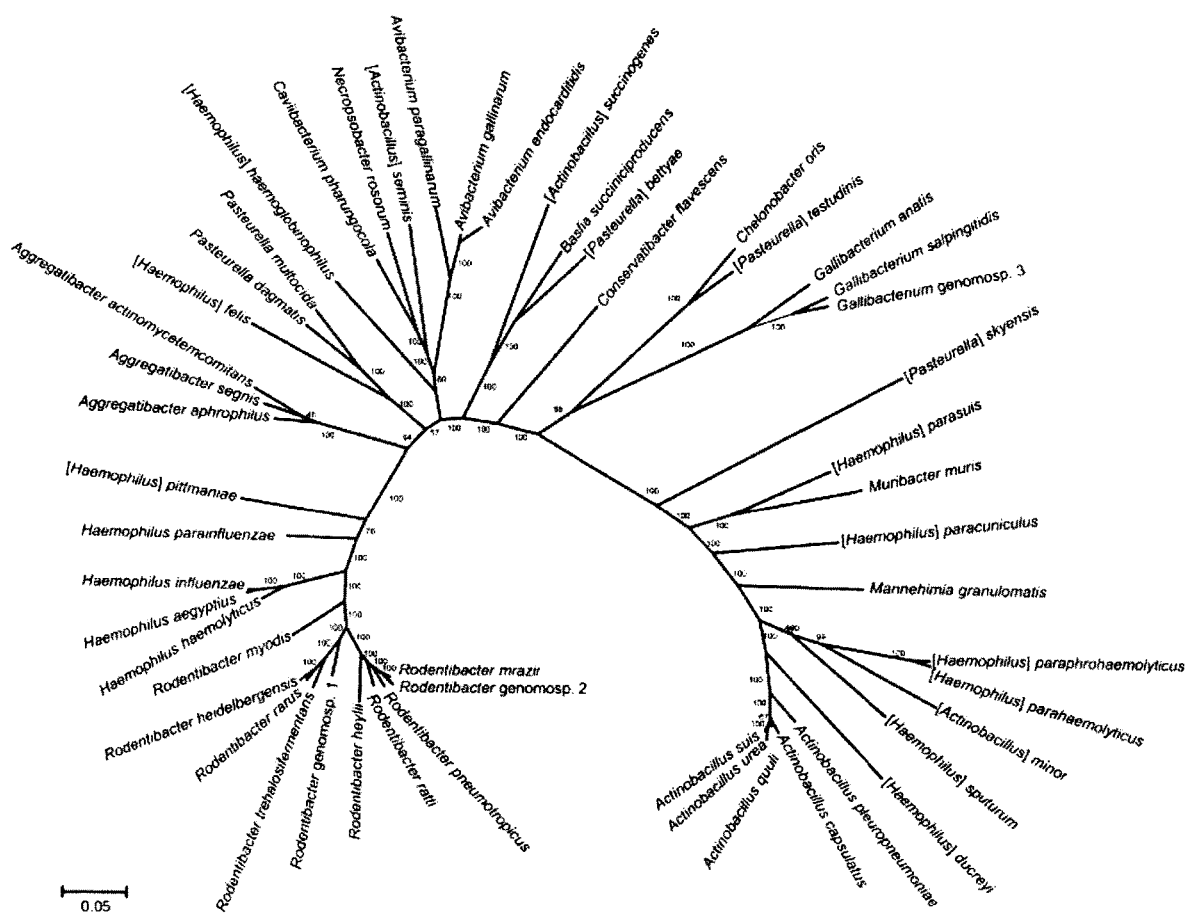

Specification includes a Sequence Listing.

(56) References Cited

OTHER PUBLICATIONS

Latham et al., "An isolate of Haemophilus haemolyticus produces a bacteriocin-like substance that inhibits the growth of nontypeable Haemophilus influenzae", Intl. J. Antimicrobial Agents, 2017, 4 pages. (Year: 2017).*
Pickering et al., "Haemophilus haemolyticus Interaction with Host Cells Is Different to Nontypeable Haemophilus influenzae and Prevents NTHi Association with Epithelial Cells", Frontiers in Cellular and Infection Microbiology, vol. 6, Article 50, 2016, pp. 1-12. (Year: 2016).*
Baer et al., "Viral Concentration Determination Through Plaque Assays: Using Traditional and Novel Overlay Systems", Journal of Visualized Experiments, vol. 93, 2014, pp. 1-10.
Christensen et al., "Classification of genera of Pasteurellaceae using conserved predicted protein sequences", J. Syst. Evol. Microbiol., vol. 68, 2018, pp. 2692-2696.
Dasaraju et al., "Chapter 93: Infections of the Respiratory Systems", Medical Microbiology 4th Edition, Ed. by Baron, 1996, 15 pages.
De Vries et al., "Genetic requirements for Morazella catarrhalis growth under iron-limiting conditions", Molecular Microbiology, vol. 87, No. 1, 2013, pp. 14-29.
Herriott et al., "Defined Nongrowth Media for Stage II Development of Competence in Haemophilus influenzae", Journal of Bacteriology, vol. 101, No. 2, 1970, pp. 517-524.
Kirkham et al., "Nasopharyngeal Carriage of Haemophilus haemolyticus in Otitis-Prone and Healthy Children", J. Clinical Microbiol., vol. 48, No. 7, 2010, pp. 2557-2559.
Kirkham et al., "A practical method for preparation of pneumococcal and nontypeable Haemophilus influenzae inocula that preserves viablity and immunostimulatory activity", BMC Research Notes, vol. 6, 2013, pp. 1-5.
Langerels et al., "Modified Lipooligosaccharide Structure Protects Nontypeable Haemophilus influenzae from IgM-Mediated Complement Killing in Experimental Otitis Media", mBio, vol. 3, Issue 4, 2012, 9 pages.
Latham et al., "An isolate of Haemophilus haemolyticus produces a bacteriocin-like substance that inhibits the growth of nontypeable Haemophilus influenzae", Intl. J. Antimicrobial Agents, 2017, 4 pages.
Martin et al., "Cross-regulation of competence pheromone production and export in the early control of transformation In *Streptococcus pneumoniae*", Molecular Microbiology, vol. 38, No. 4, 2000, pp. 867-878.
Pickering et al., "Haemophilus haemolyticus Interaction with Host Cells Is Different to Nontypeable Haemophilus Influenzae and Prevents NTHi Association with Epithelial Cells", Frontiers in Cellular and Infection Microbiology, vol. 6, Article 50, 2016, pp. 1-12.
Price et al., "Haemophilus influenzae: using comparative genomics to accurately identify a highly recombinogenic human pathogen", BMC Genomics, vol. 16, 2015, 10 pages.
Reed, "Chapter 84: Respiratory Tract Infections: A Clinical Approach", Molecular Medical Microbiology, 2015, pp. 1499-1506.
Schillinger et al., Antibacterial Activity of Lactobacillus sake Isolated from Meat, Applied and Environmental Microbiology, vol. 55, No. 8, 1989, pp. 1901-1906.
Scott et al., "Protection against maternal infection-associated fetal growth restriction: proof-of-concept with a microbial-derived immunomodulator", Mucosal Immunology, vol. 10, No. 3, 2017, pp. 789-801.
Wiertsema et al., "Predominance of nontypeable Haemophilus influenzae in children with otitis media following Introduction of a 3+0 pneumococcal conjugate vaccine schedule", Vaccine, vol. 29, 2011, pp. 5163-5170.
Williams et al., "Serum Resistance in an Invasive, Nontypeable Haemophilus influenzae Strain", vol. 69, No. 2, 2001, pp. 695-705.
Zoorob et al., "Antibiotic Use in Acute Upper Respiratory Tract Infections", Am Fam Physician, vol. 86, No. 9, 2012, pp. 817-822.

* cited by examiner

Christensen and Bisgaard, 2018

SEQUENCE LISTING

```
<160> NUMBER OF SEQ ID NOS: 8

<210> SEQ ID NO 1
<211> LENGTH: 19
<212> TYPE: DNA
<213> ORGANISM: Artificial Sequence
<220> FEATURE:
<223> OTHER INFORMATION: Primer

<400> SEQUENCE: 1
gccgctctag aactagtgg                                                        19

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
gatacccctc gaattgacgc                                                       20

<210> SEQ ID NO 3
<211> LENGTH: 20
<212> TYPE: DNA
<213> ORGANISM: Artificial Sequence
<220> FEATURE:
```

```
<223> OTHER INFORMATION: Primer

<400> SEQUENCE: 3
tcattttaga cggtgcgatg                                                    20

<210> SEQ ID NO 4
<211> LENGTH: 39
<212> TYPE: DNA
<213> ORGANISM: Artificial Sequence
<220> FEATURE:
<223> OTHER INFORMATION: Primer

<400> SEQUENCE: 4
ccactagttc tagagcggcc acgggaagcg ttagaggta                                39

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
cacacccaac cacttcatca                                                    20

<210> SEQ ID NO 6
<211> LENGTH: 40
<212> TYPE: DNA
<213> ORGANISM: Artificial Sequence
<220> FEATURE:
<223> OTHER INFORMATION: Primer

<400> SEQUENCE: 6
gcgtcaattc gagggtatc accacaaact caacccaagc                               40

<210> SEQ ID NO 7
<211> LENGTH: 19
<212> TYPE: DNA
<213> ORGANISM: Artificial Sequence
<220> FEATURE:
<223> OTHER INFORMATION: Primer

<400> SEQUENCE: 7
tcggcaattg gtacgtttt                                                     19

<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8
caatggttca gatacgacga c                                                  21
```

TREATING OR PREVENTING RESPIRATORY INFECTION

CROSS-REFERENCE TO RELATED APPLICATIONS

This application claims priority to U.S. Provisional Application No. 63/033,442, filed on Jun. 2, 2020, the entire contents of which are incorporated by reference herein.

REFERENCE TO SEQUENCE LISTING

This application is filed with a Computer Readable Form of a Sequence Listing in accord with 37 C.F.R. § 1.821(c). The text file submitted by EFS, "043153-9368-US02_sequence_listing_27 May 2021_ST25," was created on May 27, 2021, has a file size of 2 Kbytes, and is hereby incorporated by reference in its entirety.

TECHNICAL FIELD

The present disclosure relates to treating or preventing respiratory infection. In particular, the present disclosure relates to methods and compositions for treating or preventing viral and/or bacterial respiratory infection in a subject.

INTRODUCTION

Respiratory tract infections (RTIs) are extremely prevalent, accounting for 20% of medical consultations and 30% of lost work days (Reed, 2015). The situation is even more dramatic in developing countries where nearly 20% of mortality in children under the age of 5 years can be attributed to RTI (Reed, 2015). Respiratory tract infections comprise infections to the upper respiratory tract and/or infections to the lower respiratory tract. Infections to the upper respiratory tract in particular, is caused by an acute infection, which includes the nose, sinuses, pharynx, or larynx. This commonly includes nasal obstruction, sore throat, tonsillitis, pharyngitis, laryngitis, epiglottitis, sinusitis, otitis media, and the common cold (Dasaraju and Liu, 1996). Viruses, for example influenza viruses, rhinoviruses, adenovirus, parainfluenza viruses, respiratory syncytial virus, enterovirus, and coronaviruses, and bacteria for example *Haemophilus influenzae, Streptococcus pneumoniae, Neisseria meningitidis, Bordatella pertussis, Moraxella catharralis, Streptococcus pyogenes, Klebsiella pneumoniae* can cause upper or lower respiratory tract infections. Viral infections can be associated with bacterial overgrowth and often lead to a secondary bacterial infection (e.g. acute bacterial rhinosinusitis, otitis media, bacterial pneumonia), which typically requires antibiotic therapy.

Currently, treatment of upper respiratory tract infections may involve the use of comfort measures (e.g. nasal suction for infants, steam or mist inhalation, nasal irrigation, getting plenty of rest and drinking plenty of fluids), use of over-the-counter medicated products (nasal sprays, decongestants, saline nose drops and analgesics), use of home food remedies (liquid concoctions which contain garlic, honey, ginger, lemon juice), taking anti-flu medications (amantadine, rimantadine, zanamivir, oseltamivir), taking antibiotics (treats only bacterial infections) and taking probiotics. Antibiotics are effective only for treating bacterial infections. Because the vast majority of respiratory illnesses are viral infections, antibiotic use will not cure or shorten the length of a viral infection (Zoorob et al. 2012). However, there are still many instances of medical practitioners prescribing antibiotics for viral respiratory infections which in effect, drives the increase in antimicrobial resistance.

Vaccines offer a preventative therapy to some viral and bacterial respiratory infections. The current use of vaccines is costly as they are expensive to manufacture, are expensive to store and transport (requires cold-chain delivery), have a limited shelf life and require trained medical personnel to administer. Additionally, vaccines are typically only effective against a specific pathogen, with limited evidence of off-target protection. There is also vaccine hesitancy, either from vaccine misinformation, fear of needles or other reasons.

What is needed is an alternative form of therapy for prevention or treatment of viral or bacterial respiratory infections that is low-cost, easy to administer and readily accessible.

SUMMARY

The inventors have found that administering an intranasal dose of a species of commensal respiratory bacteria from the family Pasteurellaceae to a subject reduces viral and/or bacterial titres and inflammation due to viral and/or bacterial infection in the respiratory tract of the subject.

A first aspect provides a method for treating or preventing a viral and/or bacterial respiratory infection in a subject, the method comprising administering to the respiratory tract of the subject an effective amount of one or more bacteria from family Pasteurellaceae.

A second aspect provides a method of reducing viral and/or bacterial titre in the respiratory tract of a subject, comprising administering to the respiratory tract of the subject an effective amount of one or more bacteria from family Pasteurellaceae.

A third aspect provides a method of preventing or reducing inflammation caused by a virus and/or bacteria in the respiratory tract of a subject, the method comprising administering to the respiratory tract of the subject an effective amount of one or more bacteria from family Pasteurellaceae.

In one embodiment, the one or more bacteria is a commensal bacteria.

In one embodiment, the one or more bacteria is a human commensal bacteria.

In one embodiment, the one or more bacteria is *Haemophilus haemolyticus*.

In one embodiment, the one or more bacteria is *Muribacter muris*.

In one embodiment, the one or more bacteria comprises a combination of two or more species of bacteria. In one embodiment, the one or more bacteria comprises a single species of bacteria.

In one embodiment, the one or more bacteria is administered to the subject prior to the subject having a viral and/or bacterial respiratory infection.

In one embodiment, the one or more bacteria is administered to the subject when the subject is infected with a viral and/or bacterial respiratory infection.

In one embodiment, the virus is influenza virus.

In one embodiment, the viral respiratory infection is caused by influenza virus.

In one embodiment, the influenza virus is influenza A virus.

A fourth aspect provides one or more bacteria from Pasteurellaceae family for use in treating or preventing viral and/or bacterial respiratory infection in a subject.

A fifth aspect provides use of one or more bacteria from Pasteurellaceae family in the manufacture of a medicament for treating or preventing viral and/or bacterial respiratory infection in a subject.

A sixth aspect provides use of one or more bacteria from Pasteurellaceae family in the manufacture of a medicament for reducing viral and/or bacterial titre in the respiratory tract of a subject.

A seventh aspect provides use of one or more bacteria from Pasteurellaceae family in the manufacture of a medicament for preventing or reducing inflammation caused by a virus and/or bacteria in the respiratory tract of a subject.

An eighth aspect provides a pharmaceutical composition comprising one or more bacteria from Pasteurellaceae family for treating or preventing a viral and/or bacterial respiratory infection in a subject.

In one embodiment of the eighth aspect, the pharmaceutical composition further comprising a pharmaceutically acceptable carrier.

In one embodiment of the eighth aspect, the pharmaceutically acceptable carrier comprises a diluent and/or excipient for nasal and/or pulmonary delivery.

In one embodiment of the eighth aspect, the one or more bacteria are lyophilised.

A ninth aspect provides a method of reducing viral and/or bacterial titre in the respiratory tract of a subject, the method comprising administering to the respiratory tract of the subject a pharmaceutical composition of the eighth aspect.

A tenth aspect provides a kit for treating or preventing a viral and/or bacterial respiratory infection and/or reducing viral and/or bacterial titre in the respiratory tract of a subject and/or reducing inflammation due to a viral infection, comprising a composition comprising one or more bacteria of the family Pasteurellaceae.

In one embodiment of the tenth aspect, the kit further comprises a pharmaceutically acceptable carrier.

In one embodiment of the tenth aspect, the pharmaceutically acceptable carrier comprises a diluent and/or excipient for nasal and/or pulmonary delivery.

In one embodiment of the tenth aspect, the kit further comprises a device adapted for nasal and/or pulmonary delivery of the pharmaceutical composition.

In one embodiment of the tenth aspect, the one or more bacteria is provided in lyophilized form.

In one embodiment of the tenth aspect, the carrier is a lyophilization excipient.

In one embodiment of the tenth aspect, the one or more bacteria is reconstituted by the carrier prior to use.

A thirteenth aspect provides a method for treating or preventing otitis media in a subject, the method comprising administering to the respiratory tract of the subject an effective amount of one or more bacteria from family Pasteurellaceae.

BRIEF DESCRIPTION OF THE DRAWINGS

FIG. 1 is a joining tree showing the phylogenetic relationship between the species of the Pasteurellaceae family (Christensen and Bisgaard, 2018). *Muribacter muris* belongs to the same family as *Haemophilus influenzae* and *Haemophilus haemolyticus.*

FIG. 2A-B are graphs showing pre-treatment of mice with a single dose of *Muribacter muris* reduces influenza A virus titres in the lungs and local inflammation in the nasal passages. FIG. 2A shows influenza virus (IAV) copies in the lung tissue of mice on Day 5 and Day 7 post influenza challenge. Mm+IAV=mice that were pre-treated with a single intrasal dose of *M. muris* (Mm). FIG. 2B shows titres (pg/mL) of innate immune signalling molecule interleukin-6 (IL-6) in nasal washes from the same mice on Day 5 and Day 7 post influenza challenge. Each circle represents an individual mouse, horizontal bars represent the median viral copy number or IL-6 titre. The dashed horizontal line represents the limit of detection (LOD) for the cytokine assay, with samples below the LOD assigned half the LOD for statistical analyses. Naïve=control mice that received no treatments. **, P<0.01 when compared between treatment groups.

FIG. 3A-D are graphs showing pre-treatment of mice with *Muribacter muris* reduces NTHi colonization and prevents development of otitis media from NTHi.

Nontypeable *Haemophilus influenzae* (NTHi) density in $\log_{10}$ CFU/ml from nasal washes and middle ear tissue homogenates of mice on day 5 (FIG. 3A and FIG. 3B) and day 7 (FIG. 3C and FIG. 3D) post challenge. Each circle represents an individual mouse. Filled black circles represent mice that did not receive *M. muris* pre-treatment prior to IAV+NTHi, open white circles represent mice that were pre-treated intranasally with a single dose of $5\times10^7$ CFU of *M. muris* on day −1 prior to IAV+NTHi (*M. muris* [Mm]+IAV+NTHi). Horizontal bars depict the median NTHi density, and the dashed line represents the limit of quantification. *, P<0.05; , P<0.01; *, P<0.001.

FIG. 4A-B are graphs showing *M. muris* pre-treatment reduces inflammation in the upper respiratory tract. Inflammatory mediator levels in nasal washes (FIG. 4A) and middle ear tissue homogenate (FIG. 4B) from mice on day 5 and day 7 post challenge. Each circle represents an individual mouse. Filled black circles represent mice in control groups given *M. muris* only (Mm), influenza A virus only (IAV), NTHi only, or in combinations. The open white circles represent mice that were pre-treated intranasally with a single dose of $5\times10^7$ CFU of *M. muris* on day −1 prior to undergoing influenza virus and NTHi challenge (*M. muris*+IAV+NTHi). Horizontal bars depict the median analyte titer in picograms per milliliter, and the dashed line represents the assay limit of detection. *, P<0.05; , P<0.01; *, P<0.001.

FIG. 5A-B are graphs showing pre-treatment of mice with *M. muris* improves clinical outcomes and reduces otitis media-induced weight loss in the NTHi otitis media model. Mean clinical score (FIG. 5A) and weight loss (FIG. 5B) for mice with (closed black circles; n=12 by day 7) or without (white circles; n=15 by day 7)*M. muris* (Mm) pre-treatment. Values are presented as the mean±standard error of the mean. D, days post challenge with influenza A virus challenge (IAV) as the reference point. NTHi was administered on day 3 and mice monitored to day 7; *, P<0.01 when compared between treatment groups.

FIG. 6 is graphs showing *M. muris* treatment induces a short-lived and local inflammatory response. Inflammatory mediator levels in nasal washes and middle ear tissue homogenate from mice following intranasal challenge with $5\times10^7$ CFU of *M. muris* on day −1. Specimens were collected on days 0, 3, 5, and 7, which were 1, 4, 6, and 8 days, respectively, after *M. muris* challenge. Each circle represents cytokine levels for an individual mouse. Horizontal bars depict the median analyte titer in picograms per milliliter, and the dashed line represents the assay limit of detection. *, P<0.05; , P<0.01; *, P<0.001.

FIG. 7 is graphs showing *M. muris*-like counts in nasal washes and middle ear tissue following intranasal challenge with *M. muris* and/or influenza virus. *M. muris*-like log CFU per milliliter counts in nasal washes and middle ear tissue homogenate from naive mice and mice intranasally treated with *M. muris* on day −1 (*M. muris*), influenza A virus on day 0 (IAV), or *M. muris* on day −1 and influenza A virus on day 0 (*M. muris*+IAV). Specimens were collected on days 0 (*M. muris* only), 3, 5, and 7. Each circle represents an individual mouse. Horizontal bars depict the median *M. muris*-like log density, and the dashed line represents the limit of quantification.

Figure 8:
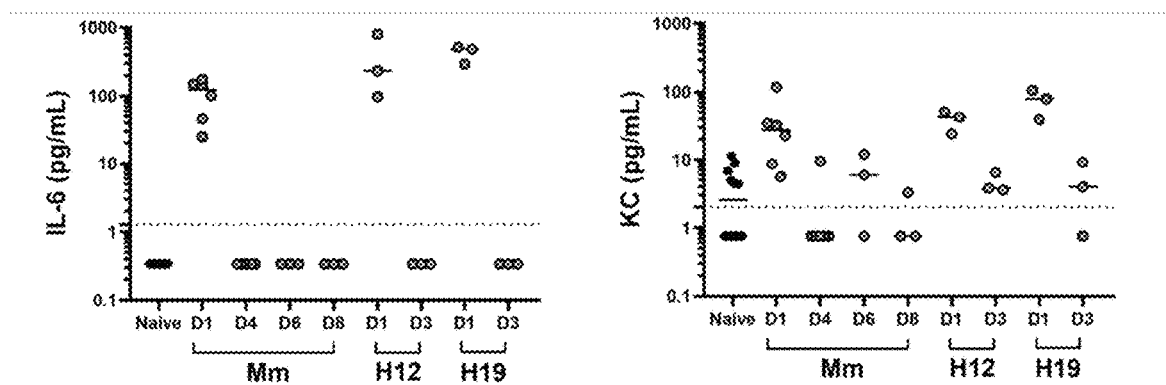

FIG. 8 is graphs showing that *Haemophilus haemolyticus* elicits the same local immune profile as *Muribacter muris* when instilled intranasally in mice. Titres (pg/mL) of innate immune signalling molecules IL-6 and KC (IL-8 homolog in mice) in nasal washes from mice intranasally treated with the same dose of either *Muribacter muris* (Mm) or *Haemophilus haemolyticus* strain 12 (H12) and strain 19 (H19) on Day 1 (D1) to Day 8 (D8) post-treatment. Each circle represents an individual mouse, horizontal bars represent the median analyte titre. The dashed horizontal line represents the limit of detection (LOD) for each assay, with samples below the LOD assigned half the LOD for statistical analyses.

Figure 9A:
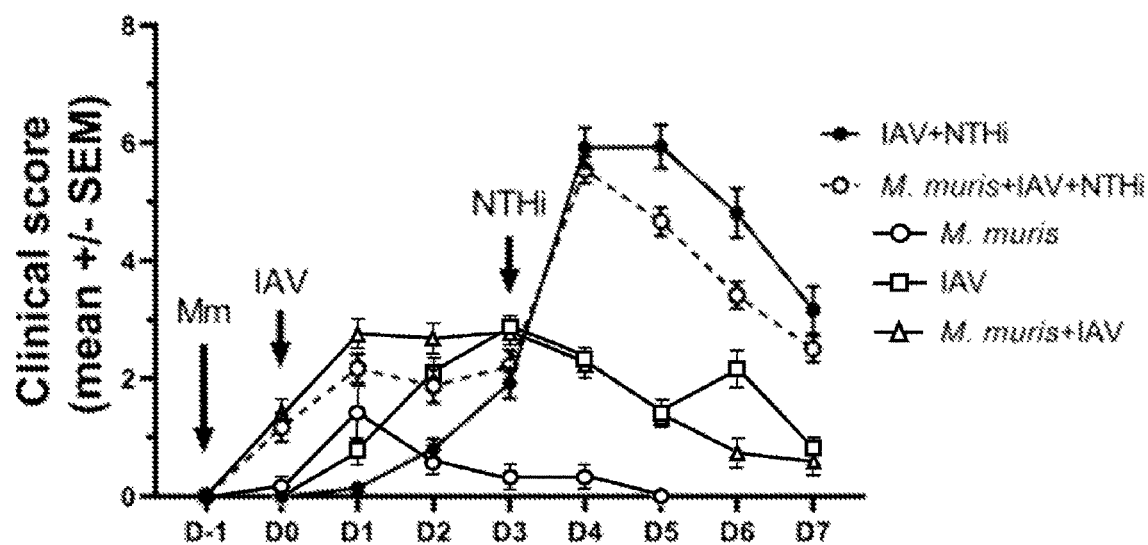
Figure 9B:
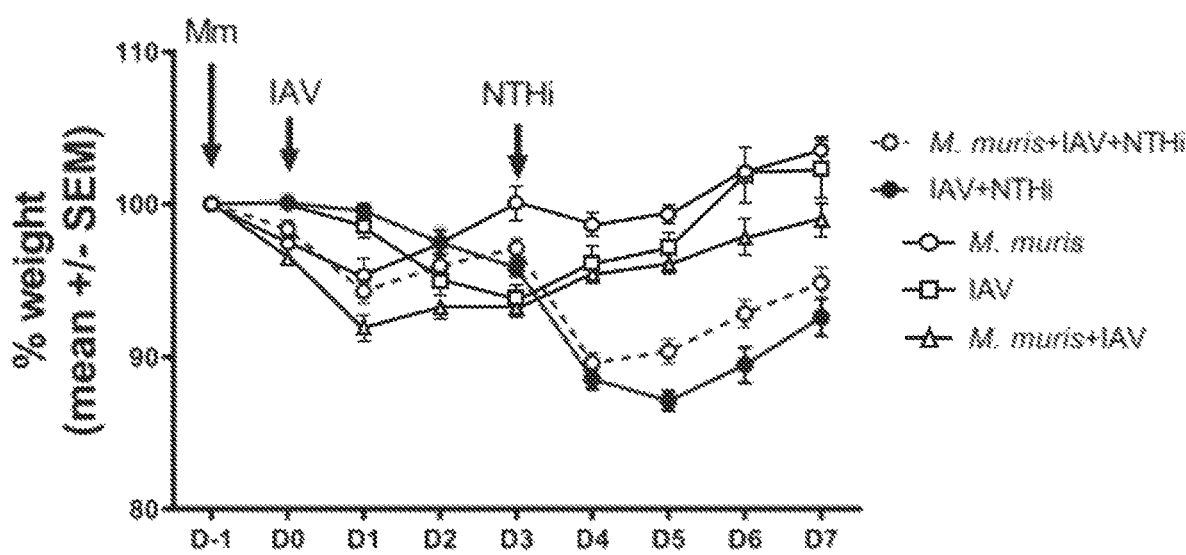

FIG. 9A-B are graphs showing pre-treatment of mice with *M. muris* had minimal impact on clinical score and weight loss. Mean clinical score (FIG. 9A) and weight loss (FIG. 9B) for all treatment groups of mice. Values are presented as the mean+/−standard error of the mean. D=Days post challenge, with influenza A challenge (IAV) as the reference point. NTHi was administered on Day 3 and mice were monitored to Day 7 (*M. muris* only to Day 4); * p<0.01 when compared between Mm+IAV+NTHi and IAV+NTHi. Black lines with filled black circles represent mice that did not receive *M. muris* (Mm) pre-treatment prior to IAV+NTHi; black dashed lines with open white circles represent mice that were pre-treated intranasally with *M. muris* on Day −1 prior to IAV+NTHi (Mm+IAV+NTHi). Black solid lines and open shapes represent control groups of mice that were treated with either *M. muris* only, IAV only or *M. muris*+IAV.

KEY TO SEQUENCE LISTING

SEQ ID NO: 1—primer PBpR412_L
SEQ ID NO: 2—primer PBpR412_R
SEQ ID NO: 3—primer R2866_1356_L1
SEQ ID NO: 4—primer R2866_1356_L2
SEQ ID NO: 5—primer R2866_1356_R1
SEQ ID NO: 6—primer R2866_1356_R2
SEQ ID NO: 7—primer R2866_1356_L1+R2866_1356_C
SEQ ID NO: 8—primer R2866_1356_L1+PBMrTn9

DETAILED DESCRIPTION

The present disclosure relates in one form to a method for treating or preventing a viral and/or bacterial respiratory infection in a subject. As described in the Examples, the inventors have found that providing bacteriotherapy in the form of a single intranasal dose of a species of commensal respiratory bacteria from the family Pasteurellaceae provides protection against viral and bacterial respiratory infection. Also described in the Examples, the inventors have found that providing bacteriotherapy in the form of a single intranasal dose of a species of commensal respiratory bacteria from the family Pasteurellaceae reduces viral and bacterial pathogen titres in the respiratory tract of a subject as well as reduces inflammation caused by a virus and/or bacterial pathogens in the respiratory tract of a subject.

The inventors have shown that a commensal bacteria from the family Pasteurallaceae can protect against not only infection from bacteria in this family (NTHi; FIG. 3), but also from viruses including influenza (FIG. 2). Without wishing to be bound by theory, the inventors believe that administering commensal bacteria of the family Pasteurellaceae activates the innate immune system and leads to a generalised protection from both viral and bacterial respiratory infections.

Over 200 different viruses can cause upper and lower respiratory infections, including, for example, rhinovirus, coronavirus, parainfluenza virus, adenovirus, enterovirus, respiratory syncytial virus (RSV), bocavirus, influenza viruses, human metapneumoviris (hMPV), orthomyxoviridae, cytomegalovirus, Epstein-Barr virus, herpes simplex virus, and morbillivirus.

Bacteria responsible for upper and lower respiratory infections include, for example, group A *Streptococcus* (*Streptococcus pyogenes*), *Haemophilus influenzae*, *Pseudomonas* spp., Mycobacteria spp., *Pasterurella* spp., *Pneumocystis* jiroveci, *Mycobacterium tuberculosis*, *Peptostreptococcus* spp., *Fusobacterium prevotella*, *Klebsiella pneumonia*, *Moraxella catarrhalis*, *Streptococcus pneumoniae*, *Chlamydophila pneumoniae*, *Mycoplasma pneumoniae*, *Legionella pneumophila*, *Staphylococcus aureus*, *Corynebacterium diphtheriae*, *Neisseria meningitidis*, *Fusobacterium necrophorum*, *Bordetella pertussis*, *Treponema pallidum*, *Chlamydia trachomatis*, *Pseudomonas aeruginosa*, *Bacillus anthracis* and *Chlamydophila psittaci*.

Upper respiratory infections are infections of the nose, sinuses, nasal cavity, pharynx or larynx and include, for example, tonsillitis, pharyngitis, rhinitis, rhinosinusitis, nasopharyngitis, laryngitis, sinusitis, laryngopharyngitis, laryngotraceheitis, larynepiglottitis, laryngotracheitis, tracheitis, otitis media, and the common cold.

In one aspect, the present invention relates to a method for treating or preventing a viral and/or bacterial respiratory infection in a subject. In one aspect, the present invention relates to a method for treating or preventing a viral respiratory infection in a subject. The method comprises administering to the respiratory tract of the subject an effective amount of one or more bacteria from family Pasteurellaceae.

In another aspect, the present invention relates to a method of reducing viral and/or bacterial titre, typically bacterial pathogen titre, in the respiratory tract of a subject, comprising administering to the respiratory tract of the subject an effective amount of one or more bacteria from family Pasteurellaceae. In another aspect, the present invention relates to a method of reducing viral titre in the respiratory tract of a subject, comprising administering to the respiratory tract of the subject an effective amount of one or more bacteria from family Pasteurellaceae.

In another aspect, the present invention relates to a method of preventing or reducing inflammation caused by a virus and/or bacteria, typically bacterial pathogen, in the respiratory tract of a subject, the method comprising administering to the respiratory tract of the subject an effective amount of one or more bacteria from family Pasteurellaceae. In another aspect, the present invention relates to a method of preventing or reducing inflammation caused by a virus in the respiratory tract of a subject, the method comprising administering to the respiratory tract of the subject an effective amount of one or more bacteria from family Pasteurellaceae.

In another aspect, the present invention relates to a method for treating or preventing a bacterial respiratory infection in a subject. The method comprises administering to the respiratory tract of the subject an effective amount of one or more bacteria from family Pasteurellaceae. In another aspect, the present invention provides a method of reducing bacterial titre, typically bacterial pathogen titre, in the respiratory tract of a subject, comprising administering to the respiratory tract of the subject an effective amount of one or more bacteria from family Pasteurellaceae. In another aspect, the present invention provides a method of preventing or reducing inflammation caused by a bacteria, typically a pathogenic bacteria, in the respiratory tract of a subject, the method comprising administering to the respiratory tract of the subject an effective amount of one or more bacteria from family Pasteurellaceae. A method for treating or preventing otitis media in a subject, the method comprising administering to the respiratory tract of the subject an effective amount of one or more bacteria from family Pasteurellaceae.

Pasteurellaceae are a family of Gram-negative bacteria including human and animal pathogens and commensals. The most important genera are *Haemophilus, Actinobacillus, Pasteurella*, and *Mannheimia*.

As used herein, "treating" means affecting a subject, tissue or cell to obtain a desired pharmacological and/or physiological effect and includes inhibiting the condition, i.e. arresting its development; or relieving or ameliorating the effects of the condition i.e., cause reversal or regression of the effects of the condition. As used herein, "preventing" means preventing a condition from occurring in a cell or subject that may be at risk of having the condition, but does not necessarily mean that condition will not eventually develop, or that a subject will not eventually develop a condition. Preventing includes delaying the onset of a condition in a cell or subject.

Any animal subject may be treated by the methods or compositions disclosed herein. As used herein, the term "subject" refers to an animal. Typically, the subject is a mammal. In one embodiment, the mammal is a human. In another embodiment, the mammal is a non-human mammal. In one embodiment, the non-human mammal is a pig.

As used herein, the terms "bacterial infection" and "viral infection" includes any stage of infection known to contribute to the pathogenesis of the bacteria or virus for example: transmission, adhesion, invasion, survival in the host.

As used herein, the term "respiratory infection" refers to an infection of the upper respiratory tract and/or lower respiratory tract of a subject.

As used herein, the term "effective amount" or a "therapeutically effective amount" means a sufficient quantity of a substance (e.g. bacteria) to treat or prevent a disease or condition (e.g., viral and/or bacterial respiratory infection) in a subject. This term is not to be construed to limit the disclosure to a specific quantity, e.g., number of bacteria; rather the present disclosure encompasses any amount of the one or more bacterial species that is sufficient to achieve the stated purpose. The amount of the one or more bacteria should not be so large as to cause adverse side effects in the subject. Generally, the amount of the one or more bacteria may be varied with the age, condition, weight, and disease history of the subject and can be determined by a person skilled in the art. The amount of the one or more bacteria can be adjusted by the individual physician in the event of any complication.

A therapeutically effective amount or effective amount or dosage is an amount or dosage of a composition at high enough levels to improve the condition to be prevented and/or treated, but low enough to avoid serious side effects (at a reasonable benefit/risk ratio), within the scope of sound medical/dental judgment. The therapeutically effective amount or dosage of a composition may vary with the particular condition being treated, the age and physical condition of the patient being treated, the severity of the condition, the duration of treatment, the nature of concurrent therapy, the specific form of the source employed, and the particular vehicle from which the composition is applied.

The compositions described herein can be applied in a therapeutically effective amount or effective amount to the mouth, oropharynx, larynx, nasal cavity, and/or fauces for the treatment and/or prevention of one or more respiratory infections. In a preferred embodiment of the present invention, the compositions described herein can be applied in a therapeutically effective amount to the nasal cavity.

The method described herein comprises administering to the subject the one or more bacteria of the family Pasteurellaceae. Typically, the one or more bacteria is a commensal bacteria of the family Pasteurellaceae. More typically, the commensal bacteria is a respiratory commensal bacteria. In one embodiment, the commensal bacteria is a human commensal bacteria. Typically, the human commensal bacteria is a human respiratory commensal bacteria. In another embodiment, the commensal bacteria is a non-human commensal bacteria. Typically, the non-human commensal bacteria is a non-human respiratory commensal bacteria. Typically, the commensal bacteria is species-matched. As used herein, a "species-matched" commensal bacteria is a bacteria which is commensal to the respiratory tract, or a part thereof, of the species of subject to which it is to be administered. For example, *Haemophilus haemolyticus* is a commensal respiratory bacteria in humans, and is therefore species matched to humans.

In another embodiment, the one or more bacteria is a single species of bacteria. In one embodiment, the one or more bacteria comprises a combination of two or more species of bacteria.

In one embodiment, the one or more bacteria is a commensal bacteria from the genus *Haemophilus*. In one embodiment, the one or more bacteria is *Haemophilus haemolyticus*.

In one embodiment, the one or more bacteria is a commensal bacteria from the genus *Muribacter*. In one embodiment, the one or more bacteria is *Muribacter muris*.

In one embodiment, the one or more bacteria is a human commensal bacteria. As used herein, the term "human commensal bacteria" refers to any strain or any species of bacteria in the "Pasteurellaceae" family that inhabits a human host. Typically, the human commensal bacteria inhabits the respiratory tract, or a part thereof, of the human host. In one embodiment, the human commensal bacteria is from the genus *Haemophilus*. In one embodiment, the human commensal bacteria is *Haemophilus haemolyticus*.

In one embodiment, the one or more bacteria is a non-human commensal bacteria. As used herein, the term "non-human commensal bacteria" refers to a strain or a species of bacteria in the "Pasteurellaceae" family that inhabits a non-human host. Typically, the non-human commensal bacteria inhabits the respiratory tract, or a part thereof, of the non-human host. In one embodiment, the non-human commensal bacteria is from the genus *Haemophilus*. In one embodiment, the non-human commensal bacteria is *Muribacter muris*. As described in the Examples, pre-treatment of mice with *M. muris* prior to challenge with influenza A/Memphis/1/71 H3N2 virus (IAV) and NTHi (*M. muris*+ IAV+NTHi group) reduced viral IAV in the lungs (FIG. 2) and bacterial NTHi titres in the nose and ears (FIG. 3).

In one embodiment, the one or more bacteria is administered to the subject prior to the subject having a viral and/or bacterial respiratory infection. In one embodiment, the one or more bacteria is administered to the subject prior to the subject having a viral respiratory infection. In one embodiment, the one or more bacteria is administered to the subject prior to the subject having a bacterial respiratory infection.

In another embodiment, the one or more bacteria is administered to the subject when the subject is infected with a viral and/or bacterial respiratory infection. In another embodiment, the one or more bacteria is administered to the subject when the subject is infected with a viral respiratory infection. In another embodiment, the one or more bacteria is administered to the subject when the subject is infected with a bacterial respiratory infection.

In one embodiment, the virus is influenza virus. In one embodiment, the viral respiratory infection is caused by influenza virus. In one embodiment, the influenza virus is influenza A virus.

In one embodiment, the bacterial pathogen is a bacterial pathogen of the genus *Haemophilus*. In one embodiment, the pathogenic *Haemophilus* bacteria is *Haemophilus influenzae*. In one embodiment, the bacterial respiratory infection is caused by a pathogenic *Haemophilus* bacteria. In one embodiment, the pathogenic *Haemophilus* bacteria is *Haemophilus influenzae* bacteria. In one embodiment, the pathogenic *Haemophilus* bacteria is *Haemophilus* parasuis.

In one embodiment, there is provided one or more commensal bacteria from Pasteurellaceae family for use in treating or preventing a viral and/or bacterial respiratory infection in a subject. In another embodiment, there is provided one or more commensal bacteria from Pasteurellaceae family for use in treating or preventing a viral respiratory infection in a subject. In another embodiment aspect, there is provided one or more commensal bacteria from Pasteurellaceae family for use in treating or preventing bacterial respiratory infection in a subject.

In one embodiment, there is provided use of one or more commensal bacteria from Pasteurellaceae family in the manufacture of a medicament for treating or preventing viral and/or bacterial respiratory infection in a subject. In another embodiment, there is provided use of one or more commensal bacteria from Pasteurellaceae family in the manufacture of a medicament for use in treating or preventing viral respiratory infection in a subject. In another embodiment, there is provided use of one or more commensal bacteria from Pasteurellaceae family in the manufacture of a medicament for use in treating or preventing bacterial respiratory infection in a subject.

In one embodiment, there is provided one or more commensal bacteria from Pasteurellaceae family for use in reducing viral and/or bacterial titre in a subject. In another embodiment, there is provided one or more bacteria from Pasteurellaceae family for use in reducing viral titre in a subject. In another embodiment, there is provided one or more bacteria from Pasteurellaceae family for use in reducing bacterial titre in a subject.

In one embodiment, there is provided one or more commensal bacteria from Pasteurellaceae family for use preventing or reducing inflammation caused by a virus and/or bacteria in the respiratory tract of a subject. In one embodiment, there is provided one or more commensal bacteria from Pasteurellaceae family for use preventing or reducing inflammation caused by a virus in the respiratory tract of a subject. In one embodiment, there is provided one or more commensal bacteria from Pasteurellaceae family for use preventing or reducing inflammation caused by a bacteria in the respiratory tract of a subject. In one embodiment, reducing inflammation caused by a virus and/or bacteria in the respiratory tract of a subject is a reduction in the level of IL-6 and/or KC and/or IL-1β in the respiratory tract of the subject. A reduction in the level of IL-6 and/or KC and/or IL-1β can be determined by, for example, determining the amount of IL-6 and/or KC and/or IL-1β in respiratory washes or swabs.

In another aspect, there is provided one or more commensal bacteria from Pasteurellaceae family for use in preventing or reducing inflammation caused by a bacteria, typically a pathogenic bacteria, in the respiratory tract of a subject.

In one embodiment, there is provided use of one or more commensal bacteria from Pasteurellaceae family in the manufacture of a medicament for reducing inflammation caused by a virus and/or bacteria in the respiratory tract of a subject. In another embodiment, there is provided use of one or more commensal bacteria from Pasteurellaceae family in the manufacture of a medicament for preventing or reducing inflammation caused by a virus in the respiratory tract of a subject. In another embodiment, there is provided use of one or more commensal bacteria from Pasteurellaceae family in the manufacture of a medicament for preventing or reducing inflammation caused by a bacteria in the respiratory tract of a subject.

Another aspect provides a method for treating or preventing otitis media in a subject, the method comprising administering to the respiratory tract of the subject an effective amount of one or more bacteria, typically commensal bacteria, from family Pasteurellaceae.

Another aspect provides a method of treating or preventing a *Haemophilus influenzae* infection in a human, the method comprising administering to the respiratory tract of the subject an effective amount of *Haemophilus haemolytica*.

Another aspect provides a method of treating or preventing a *Haemophilus* parasuis infection in a non-human, typically a pig, the method comprising administering to the respiratory tract of the subject an effective amount of *Muribacter muris*.

In one aspect, there is provided a pharmaceutical composition comprising one or more bacteria from family Pasteurellaceae family for treating or preventing a viral and/or bacteria respiratory infection in a subject. In another aspect, there is provided a pharmaceutical composition comprising one or more bacteria from family Pasteurellaceae family for treating or preventing a viral respiratory infection in a subject. In another aspect, there is provided a pharmaceutical composition comprising one or more bacteria from family Pasteurellaceae family for treating or preventing a bacterial respiratory infection in a subject. Typically, the one or more bacteria are commensal bacteria. Typically, the commensal bacteria are human commensal bacteria.

In one form, the one or more bacteria are provided in the form of a pharmaceutical composition. The pharmaceutical composition may be formulated for any suitable route of administration to the respiratory tract. In a preferred embodiment, the composition is formulated as a pharmaceutical composition for intranasal administration, for example as an aerosol, a powder, liquid or an ointment. In one embodiment, the one or more bacteria are lyophilised.

The bacteria described herein may be formulated as a pharmaceutical composition. The composition typically comprises the one or more bacteria in a pharmaceutically acceptable carrier. Methods for the formulation with pharmaceutical carriers are known in the art and are described in, for example, Remington's Pharmaceutical Science, (17th ed.

Mack Publishing Company, Easton, Pa. 1985); Goodman & Gillman's: The Pharmacological Basis of Therapeutics (11th Edition, McGraw-Hill Professional, 2005).

Administration of the pharmaceutical composition to subject is typically intranasal. Compositions suitable for intranasal use include sterile aqueous solutions or dispersions and sterile powders for the extemporaneous preparation of sterile injectable solutions or dispersions. The pharmaceutically acceptable carrier can be a solvent or dispersion medium containing, for example, water, ethanol, polyol (for example, glycerol, propylene glycol, liquid polyethylene glycol and the like), suitable mixtures thereof, and vegetable oils. In many cases it will be preferable to include isotonic agents, for example, sugars or sodium chloride.

In one embodiment, the pharmaceutical composition comprises a pharmaceutically acceptable carrier. In one embodiment, the carrier comprises a diluent and/or excipient for nasal and/or pulmonary delivery.

The compositions described herein can comprise a pharmaceutically acceptable or nutritionally acceptable carrier. The carrier is physiologically compatible with the area of the subject to which it is administered. Carriers can be comprised of solid-based, dry materials for formulation into tablet, capsule, lozenge, liquid or powdered form. A carrier can also be comprised of liquid or gel-based materials for formulations into liquid, and gel forms. The composition of the carrier can be varied so long as it does not interfere significantly with the therapeutic activity of the bacterial strains of the invention. A carrier can be a sugar alcohol such as erythritol, lactitol, maltitol, mannitol, sorbitol, and xylitol.

Acceptable carriers, diluents and adjuvants are nontoxic to recipients and are preferably inert at the dosages and concentrations employed, and include water, buffered water, saline solutions such as, for example, normal saline or balanced saline solutions such as Hank's or Earle's balanced solutions), glycine, hyaluronic acid etc., buffers such as phosphate, citrate, or other organic acids; antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as xylitol, mannitol or sorbitol.

However, it will be appreciated that the formulation of the one or more bacteria to be administered will vary according to the agent, route of administration and formulation (e.g., solution, emulsion, capsule) selected. An appropriate pharmaceutical composition comprising the agent can be prepared in a physiologically acceptable carrier. A mixture of agents can also be used. For solutions or emulsions, suitable carriers include, for example, aqueous or alcoholic/aqueous solutions, emulsions or suspensions, including saline and buffered media.

In one aspect, the present invention provides a method of reducing viral and/or bacterial titre in the subject, the method comprising administering to the subject the pharmaceutical composition of the present invention. In another aspect, the present invention provides a method of reducing viral titre in the subject, the method comprising administering to the subject the pharmaceutical composition of the present invention.

In another aspect, the present invention provides a method of reducing bacterial titre in the subject, the method comprising administering to the subject the pharmaceutical composition of the present invention.

As used herein, the term "viral titre" refers to the number of viral particles present at a location. The viral titre may be determined by methods known in the art, such as for example, using plaque-based assays or quantitative reverse transcription polymerase chain reaction (qRTPCR). Viral plaque assays determine the number of plaque forming units (pfu) in a virus sample, which is one measure of virus quantity. As used herein, the term "bacterial titre" is taken to mean the estimated calculated number of bacterial cells in a sample measured in either colony-forming units (CFU, cfu, Cfu) using methods known in the art, for example, a viable count assay or genome copies by quantitative PCR. CFU refer to the number of individual colonies of any microorganism that grow on a plate of media. This value in turn represents the number of bacteria capable of replicating as they have formed colonies on the plate. There is a CFU formula which involves sampling. Calculation of CFU are conducted using methods well known in the art. As used herein, the term "titre" and "titer" are used interchangeably and are taken to have the same meaning.

The dose for intranasal administration may be in the range of about $1\times10^3$ CFU/200 µl to about $1\times10^{10}$ CFU/200 µl. The dose may be at least $1\times10^3$ CFU/200 µl, at least $1\times10^4$ CFU/200 µl, at least $1\times10^5$ CFU/200 µl, at least $1\times10^6$ CFU/200 µl, or at least $1\times10^7$ CFU/200 µl, at least $1\times10^8$ CFU/200 µl, or at least $1\times10^9$ CFU/200 µl. The dose may be less than $1\times10^{10}$ CFU/200 µl, less than $1\times10^9$ CFU/200 µl, less than $1\times10^8$, less than $1\times10^7$ CFU/200 µl, less than $1\times10^6$ CFU/200 µl, less than $1\times10^5$ CFU/200 µl, or less than $1\times10^4$ CFU/200 µl. Typically, the dose for intranasal administration is about $1\times10^4$ CFU/200 µl to $1\times10^9$ CFU/200 µl. Typically, the dose for intranasal administration is about $1\times10^5$ CFU/200 µl to $1\times10^8$ CFU/200 µl. Typically, the dose for intranasal administration is about $1\times10^3$ CFU/200 µl. Typically, the dose for intranasal administration is about $1\times10^4$ CFU/200 µl. Typically, the dose for intranasal administration is about $1\times10^5$ CFU/200 µl. Typically, the dose for intranasal administration is about $1\times10^6$ CFU/200 µl. Typically, the dose for intranasal administration is about $1\times10^7$ CFU/200 µl. Typically, the dose for intranasal administration is about $1\times10^8$ CFU/200 µl. Typically, the dose for intranasal administration is about $1\times10^9$ CFU/200 µl. Typically, the dose for intranasal administration is about $1\times10^{10}$ CFU/200 µl.

In one aspect, the present invention provides a kit for treating or preventing a viral and/or bacterial respiratory infection and/or for reducing viral and/or bacterial titre and/or preventing or reducing inflammation caused by a virus and/or bacteria in the respiratory tract of a subject, the kit comprising a composition comprising one or more bacteria of the family Pasteurellaceae. In one embodiment, the kit further comprises a pharmaceutically acceptable carrier. The pharmaceutical carrier is as described herein. In one embodiment, the pharmaceutically acceptable carrier comprises a diluent and/or excipient for nasal and/or pulmonary delivery.

In one embodiment, the kit further comprises a device adapted for nasal and/or pulmonary delivery of the pharmaceutical composition comprising the one or more bacteria and carrier. In one embodiment, the kit further comprises a device adapted for nasal delivery of the composition comprising the one or more bacteria and carrier. In one embodiment, the kit further comprises a device adapted for pulmonary delivery of the composition comprising the one or more bacteria and carrier.

In one embodiment, the kit comprises the one or more bacteria in lyophilized form. In one embodiment, the carrier is a lyophilization excipient. In one embodiment, the kit comprises the one or more bacteria in a liquid. In one embodiment, the one or more bacteria is reconstituted in the carrier prior to use.

A composition of the invention can be packaged and, in turn, a plurality of the packaged compositions can be provided in a storage container or outer package or carton. The kit may comprise instructions for use, such as instructions for administration of the one or more bacteria and carrier to a subject for: treating or preventing viral respiratory infection; treating or preventing bacterial respiratory infection; reducing viral titre; reducing bacterial titre; preventing or reducing inflammation caused by a virus in the respiratory tract; or preventing or reducing inflammation caused by a bacteria in the respiratory tract, in a subject.

Unless specifically defined otherwise, all technical and scientific terms used herein shall be taken to have the same meaning as commonly understood by one of ordinary skill in the art (e.g., in microbiology, bacterial cell culture, molecular genetics, immunology, immunohistochemistry, protein chemistry, biochemistry, and chemistry).

Unless otherwise indicated, the bacterial, genetic, recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al., (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

As used herein, the singular forms of "a", "and" and "the" include plural forms of these words, unless the context clearly dictates otherwise. For example, reference to "a bacteria" or "a bacterium" refers a plurality of that bacteria.

The term "and/or", e.g., "X and/or Y" shall be understood to mean either "X and Y" or "X or Y" and shall be taken to provide explicit support for both meanings and for either meaning.

The term "about" as used herein refers to a range of +/−10% of the specified value. For the avoidance of doubt, the term "about" is also to be taken to provide explicit support for the exact number that follows (e.g., the term "about 10" is to be taken to provide explicit support for 10 itself).

It will be appreciated by persons skilled in the art that numerous variations and/or modifications may be made to the invention as shown in the specific embodiments without departing from the scope of the invention as broadly described. The present embodiments are therefore, to be considered in all respects as illustrative and not restrictive.

All publications discussed and/or referenced herein are incorporated herein in their entirety. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

In order to exemplify the nature of the present invention such that it may be more clearly understood, the following nonlimiting examples are provided.

EXAMPLES

In this study, the inventors set out to investigate whether intranasal pre-treatment of mice with a human commensal bacteria can be used to reduce viral and/or bacterial titres in the respiratory tract. The inventors also set out to investigate whether intranasal pre-treatment of mice with a human commensal bacteria can be used to reduce inflammation caused by a virus and/or bacteria in the respiratory tract.

Example 1

Materials and Methods
Sources of Microorganisms Used in this Study
Sources of microorganisms used in this study are detailed in Table 1 below.

TABLE 1

Strains of microorganisms used in this study.

| Species | Strain (reference/source) |
| --- | --- |
| Nontypeable *Haemophilus influenzae* | R2866 (Williams et al. 2001) |
| Nontypeable *Haemophilus influenzae* | R2866 Spec$^R$ (supplied by Dr Jeroen Langereis) |
| Influenza A virus | A/Memphis/1/71 H3N2 (supplied by Alex Larcombe) |
| *Muribacter muris* | TKI (this study) |
| *Haemophilus haemolyticus* | H12 and H19 (Kirkham et al. 2010) |

Bacterial Inoculum
Standard inoculum of mid-log phase NTHi 2866 Spec$^R$ was prepared in 1 ml aliquots and stored as previously described (Kirkham et al. 2013), with the exception that 0.1 mg/ml spectinomycin was added to the culture medium.

*M. muris* was isolated from the respiratory tract of a mouse in our animal facility by plating a nasal wash onto chocolate agar plates and selecting *Haemophilus*-like colonies. Species identity of a selected isolate (*M. muris* TKI) was confirmed by sequencing of the 16S gene at the Australian Genome Research Facility in Melbourne, Australia.

*H. haemolyticus* was isolated from the nasopharynx Western Australian children participating in the GROMIT study (Wiertsema et. al 2011), which investigated the microbiology of recurrent otitis media in Western Australia and led to the isolation of *H. haemolyticus* strains from the nasopharynx of healthy and otitis-prone children (Kirkham et al. 2010). H12 and H19 are fully sequenced (Price et al. 2015) and efficiently attaches to respiratory epithelial cells with low potential for invasion (Pickering et al. 2016). These strains also elicit minimal inflammation from epithelial cells in vitro (Pickering et al. 2016) and have the same immune profile as *M. muris* when intranasally administered to mice (FIG. 8). H12 and H19 tolerate long-term cryopreservation at −80° C. in single-dose vials, making them suitable for preparation of accurate inoculum doses. H12 is sensitive to a range of antibiotics (trimethoprim, cotrimoxazole and penicillin G) as is strain H19, which is also sensitive to Erythromycin. Standard inoculum of *M. muris* was prepared by picking 3 colonies from an overnight chocolate agar plate and seeding into 15 ml culture medium (heart infusion broth supplemented with 44 ml/liter glycerol, 30 mg/liter hemin, and 10 mg/liter NAD). The culture was incubated at 37° C. with shaking to mid-log phase (optical density at 600 nm [$OD_{600}$] was between 0.55 and 0.65), then 20% heat-inactivated fetal calf serum was added, and 1-ml single-use aliquots of *M. muris* TKI were prepared and stored in cryovials at −80° C. The number of CFU for each inoculum was determined after at least 24 h storage at negative 80° C. as previously described (Kirkham et al. 2013). Viability of the frozen inoculum was assessed over the study period and found to remain stable for at least 12 months.

Standard inoculum of *H. haemolyticus* was prepared by picking 3 colonies from an overnight chocolate agar plate and seeding into 50 mL culture media (GC Medium, ATCC medium 814, supplemented with 80 mg/liter Hemin instead of haemoglobin). The culture was incubated at 37° C. with 5% $CO_2$ with shaking to mid-log phase ($OD_{600}$ nm between 0.55 and 0.65), then 20% glycerol was added and 1 ml single-use aliquots of *H. haemolyticus* were prepared and stored in cryovials at −80° C.

The number of colony forming units (CFU) for each inoculum was determined after at least 24 h storage at −80° C. as previously described (Kirkham et al. 2013). Viability of the frozen inoculum was assessed over the study period and found to remain stable for all strains tested for at least 12 months.

To prepare inoculum (Mm or Hh) on the day of treatment, single use vials were rapidly defrosted for 2 minutes in a 37° C. water bath and then centrifuged at maximum speed in a benchtop centrifuge for 3 minutes to pellet the bacteria and remove the cyropreservant. Then bacteria were washed 3 times in sterile phosphate buffered saline. The bacteria were then resuspended in sterile phosphate buffered saline to the desired concentration of $5×10^9$ CFU/mL, 10 µL was then used as the dose administered per animal ($5×10^7$ CFU).

Influenza Virus

For preparation of the influenza virus inoculum, influenza A/Memphis/1/71 H3N2 virus (IAV) was subpassaged through Madin-Darby canine kidney (MDCK) cells (NBL-2, ATCC CCL-34) in Dulbecco's modified Eagle's medium (DMEM; Gibco, Sydney, Australia), then harvested from tissue culture supernatant, and viral titers were determined by plaque assay as previously described (Baer and Kehn-Hall, 2014). Viral stocks were stored at −80° C.

Construction of NTHi R2866 Spec$^r$

The NTHi R2866 Spec$^r$ mutant was generated by allelic exchange of pseudogene R2866_1356 with a spectinomycin resistance cassette that was amplified from plasmid pR412 (Martin et al. 2000) with primers PBpR412_L (5'-GCCGCTCTAGAACTAGTGG-3'; SEQ ID NO: 1) and PBpR412_R (5'-GATACCCCTCGAATTGACGC-3'; SEQ ID NO: 2). The left flanking region of the R2866_1356 gene was amplified with primers R2866_1356_L1 (5'-TCATTT-TAGACGGTGCGATG-3'; SEQ ID NO: 3) and R2866_1356_L2 (5'-CCACTAGTTCTAGAGCGGC-CACGGGAAGCGTTAGAGGTA-3'; SEQ ID NO: 4) from genomic DNA prepared from NTHi strain R2866 (Williams et al. 2001). The right flanking region of the R2866_1356 gene was also amplified from R2866 genomic DNA using primers R2866_1356_R1 (5'-CACACCCAACCACTT-CATCA-3'; SEQ ID NO: 5) and R2866_1356_R2 (5'-GCGTCAATTCGAGGGGTATCACCACAAACT-CAACCCAAGC-3'; SEQ ID NO: 6). Primers R2866_1356_L2 and R2866_1356_R2 contain overlapping regions (in bold) with the spectinomycin cassette for the construction of a megaprimer PCR product consisting of the R2866_1356 left flanking region, spectinomycin cassette, and the R2866_1356 right flanking region. The NTHi R2866_1356 gene deletion mutant was obtained by transformation of the megaprimer PCR product using the method of Herriott et al. 1970 and selected by plating onto brain heart infusion (BHI) agar plates containing 150 pg/ml of spectinomycin. The gene deletion mutant was validated by PCR with primer sets R2866_1356_L1+R2866_1356_C (5'-TCGGCAATTGGTACGTTTT-3'; SEQ ID NO: 7) and R2866_1356_L1+PBMrTn9 (5'-CAATGGTTCAGA-TACGACGAC-3'; SEQ ID NO: 8) (de Vries et al. 2013), which detect the presence of the R2866_1356 gene or spectinomycin cassette, respectively. Gene deletions were crossed back to the wild-type strain using chromosomal DNA from the mutant strains as the donor during transformation.

Animals

All animal experiments were approved by the Telethon Kids Institute Animal Ethics Committee, Perth, Australia (number A302). Female specific-pathogen-free BALB/c mice were obtained from the Animal Resources Centre (Perth, Australia). Experiments were conducted in sets of 12 to 15 mice, ensuring representation from each group at each time point.

NTHi Otitis Media Model

Viral coinfection is required for reliable development of NTHi otitis media infection in mice using the ascension model (Langereis et al. 2012). Briefly, 6- to 8-week-old female BALB/c mice were inoculated intranasally with $1×10^4$ PFU IAV in a volume of 10 µl. At 72 h after IAV challenge, mice were intranasally administered $5×10^7$ CFU of NTHi R2866 Spec$^r$ in 10 µl of phosphate-buffered saline (PBS). For the groups pretreated with *M. muris*, mice received intranasal inoculation of $5×10^7$ CFU of *M. muris* TKI on day −1. Mice were monitored, weighed, and clinically assessed each day. Clinical disease scores were assessed as previously described (Scott et al. 2017)) using a scale ranging from 0 to 20 according to the following criteria: score 0=normal appearance, healthy, and active; score 1 to 5=barely ruffled fur, mildly/intermittent hunched appearance, and otherwise healthy; score 6 to 10=moderately ruffled fur, elevated respiratory rate, hunched appearance with a crab-like gait, intermittent stillness, and reduction of curious behavior; and score 11 to 20=ruffled fur, labored breathing, hunched appearance with a crab-like gait, and unresponsive to stimuli. Additional control groups included no treatment at all (naive), *M. muris* only, IAV only, NTHi only, and *M. muris*+IAV. Treatment groups, sample size, and experimental time points are detailed in Table 2 below.

TABLE 2

Treatment groups, sample sizes, and number of mice culled at each time point.

| Group | Timepoint (no. of mice culled) | | | | | Total no. in sample |
|---|---|---|---|---|---|---|
| | Day −1 | Day 0 | Day 3 | Day 5 | Day 7 | |
| Naïve controls | 3 | 3 | 3 | 3 | 3 | 12 |
| M.muris only | | 6 | 6 | 3 | 3 | 18 |
| IAV only | | | 6 | 6 | 6 | 18 |
| NTHi only | | | | 6 | 6 | 12 |
| M.muris + IAV | | | 6 | 8 | 9 | 23 |
| IAV + NTHi | | | | 15 | 21 | 36 |
| M.muris + IAV + NTHi | | | | 12 | 12 | 24 |

Specimen Collection and Processing

Nasal washes and middle ear bullae were collected immediately post-mortem and stored on ice. The nasal washes were conducted by lavaging the nares with 0.1 ml PBS. Middle ear tissue (combined from both ears of a mouse) was mechanically homogenized in 0.5 ml PBS using hand-held sterile plastic pestles (Interpath) until all tissue was disrupted. Nasal washes and middle ear tissue homogenates were serially diluted in PBS and spotted onto chocolate agar plates with and without an overlay of 200 µl of 10 mg/ml spectinomycin (to select for the NTHi Spec$^r$ strain). Remaining middle ear homogenate and nasal washes were centrifuged at 13,000 rpm for 10 min at 4° C. to remove cell debris. The supernatants were filtered using 0.2-µm syringe filters and stored in aliquots at −80° C. for subsequent measurement of inflammatory mediators.

Measurement of Inflammatory Mediators in Nasal Washes and Middle Ear Tissue

Stored supernatants from nasal washes and middle ear tissue homogenates were tested using a Bio-Rad express assay 5-plex murine cytokine/chemokine magnetic bioplex kit to measure IFN-γ, IL-1β, IL-6, KC, and IL-10 on the BioPlex 2000 (Bio-Rad) according to the manufacturer's instructions. Where cytokine titers were below the limit of detection (LOD), half of the value of the lowest standard was assigned to permit statistical analysis. The LOD of each cytokine was as follows: IFN-γ=0.94 pg/ml, IL-1β=1.79 pg/ml, IL-6=0.68 pg/ml, KC=1.51 pg/ml, and IL-10=4.62 pg/ml.

Statistical Analysis

Mann-Whitney U tests were applied to nonparametric data (bacterial counts, CFU/ml; cytokine levels, pg/ml), with a P value of <0.05 considered significant. Fisher's exact testing was used for categorical analyses (development of otitis media). Mean clinical scores and percent weight loss were compared by Student's t test.

Example 2

Figure 2A:
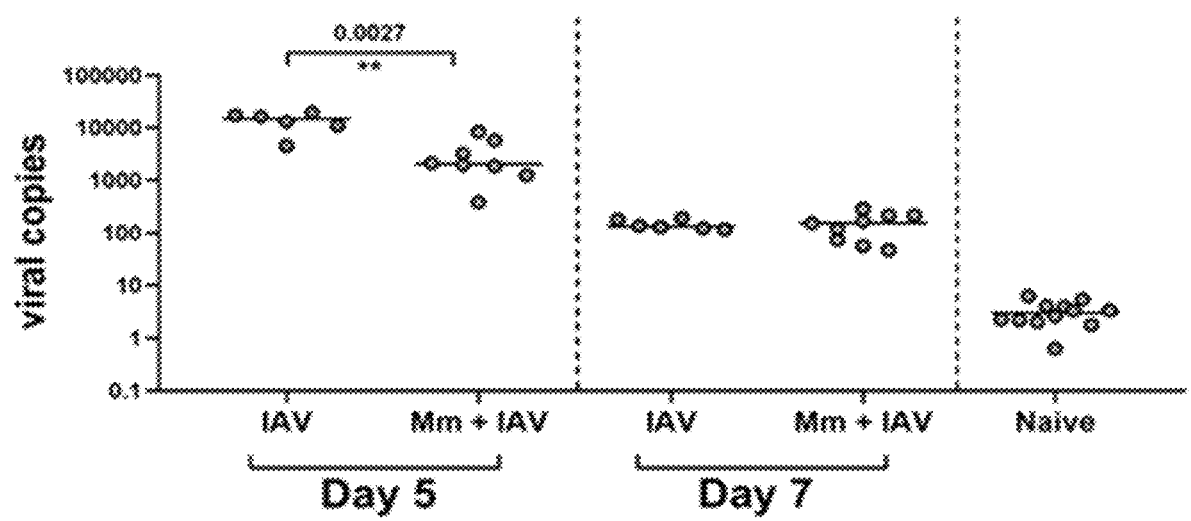
Figure 2B:
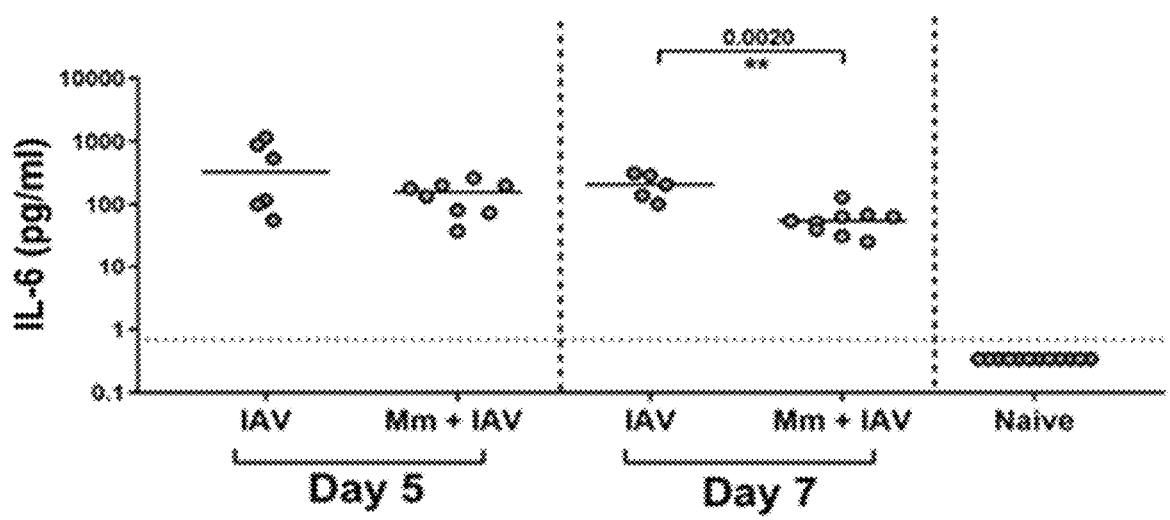

Intranasal Treatment of Mice with *M. muris* can Reduce Influenza Titres in the Lungs Intranasal pre-treatment of mice with a single dose of *M. muris* prior to challenge with influenza A/Memphis/1/71 H3N2 virus resulted in reduced influenza titres in the lung by 10-fold on day 5 post influenza challenge, p=0.0027 (FIG. 2A). Pre-treated mice also had 10-fold lower levels of the innate immune signalling molecule interleukin-6 (IL-6) in nasal washes on day 7 post influenza challenge, p=0.0020 (FIG. 2B, and data also shown in FIG. 4A as these mice were the controls in the NTHi otitis media model: Mm+IAV and Mm only).

Example 3

Figure 3A:
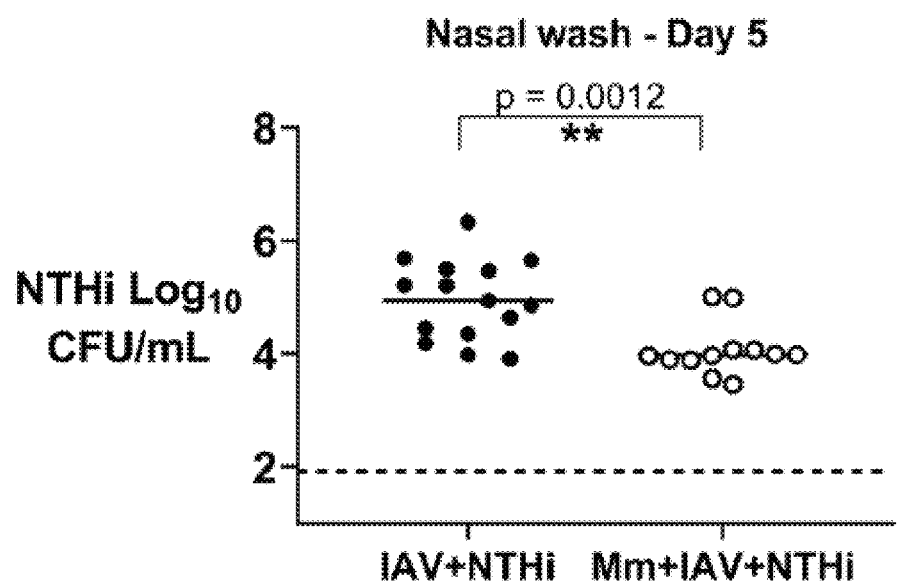
Figure 3B:
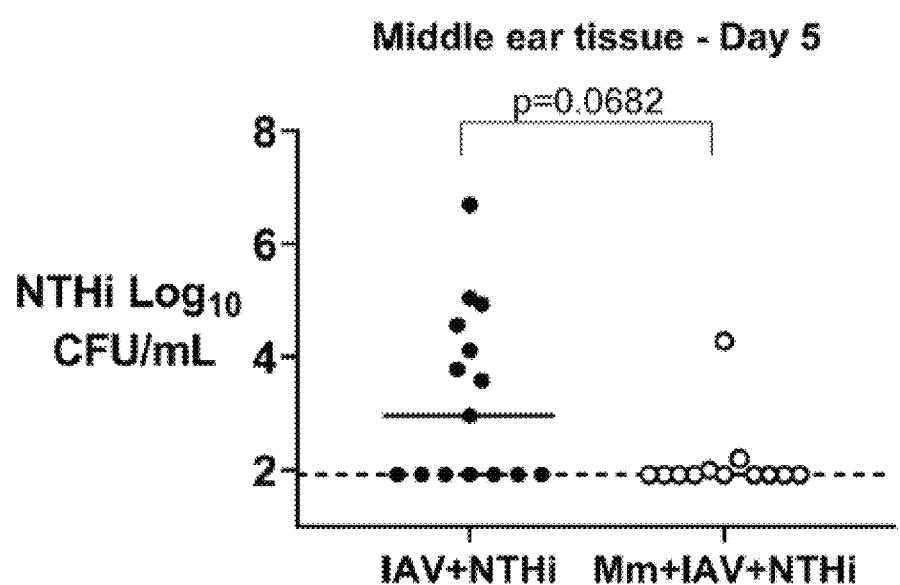
Figure 3C:
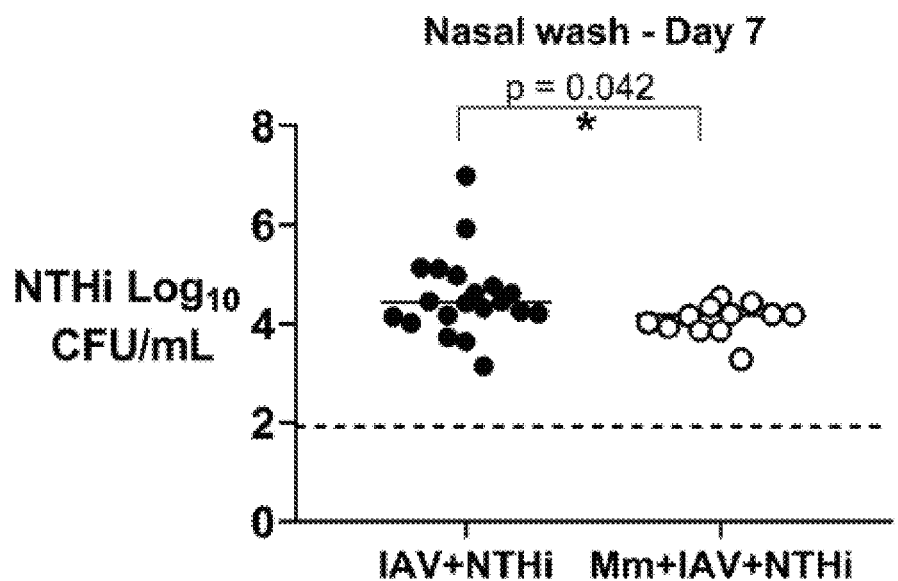
Figure 3D:
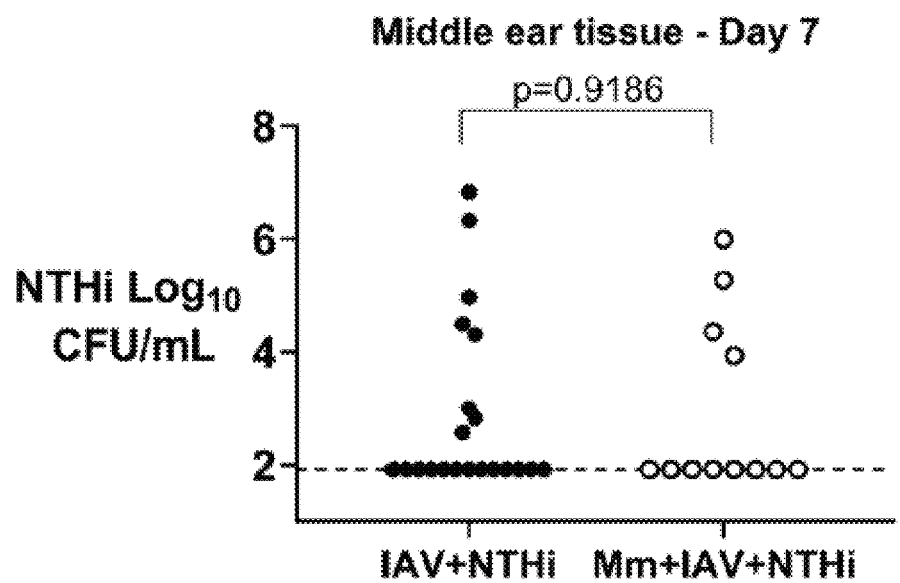

Intranasal Treatment of Mice with *M. muris* can Reduce NTHi Colonization and Prevent Development of NTHi Otitis Media Intranasal administration of 5×10$^7$ CFU of *M. muris* to mice prior to challenge with influenza A/Memphis/1/71 H3N2 virus (IAV) and NTHi (*M. muris*+IAV+NTHi group) reduced the NTHi density recovered from the nose of mice on day 5 from a median log 4.94 CFU/ml (95% confidence interval [CI] of median 4.36 to 5.50) to a median log 3.97 (95% CI, 3.88 to 4.08) when compared with that of no pre-treatment (IAV+NTHi group; P<0.001) (FIG. 3A). *M. muris* pre-treatment also prevented development of NTHi otitis media by day 5, with only 1 out of 12 (8%)*M. muris*-treated mice developing NTHi otitis media compared with 53% (8/15) of mice given no *M. muris* pre-treatment (P=0.019) (FIG. 3B). The median density of NTHi in the middle ear on day 5 reduced from median log 2.96 (95% CI, 1.92 to 4.56) to median log 1.92 (95% CI, 1.92 to 2.00) (P=0.068). By day 7, the impact of *M. muris* pre-treatment on NTHi colonization was less evident with a lower significant decrease in median NTHi density in nasal washes from *M. muris*-pre-treated versus untreated mice (log 4.17 [95% CI, 3.87 to 4.34] versus log 4.43 [95% CI, 4.17 to 4.77]; P=0.042) (FIG. 3C). There was no difference in the proportion of mice that had otitis media by day 7, with 4 out of 12 (33%)*M. muris*-treated mice developing NTHi otitis media compared to 8 out of 21 (38%) mice with no *M. muris* pre-treatment (P>0.999) (FIG. 3D). The median log density of NTHi recovered from the middle ear on day 7 was the same for each group at log 1.92 (*M. muris* treated=1.92 [95% CI, 1.92 to 4.35] and untreated=1.92 [95% CI, 1.92 to 3.00]; P=0.981), which is at the limit of quantification.

Example 4

Figure 4A:
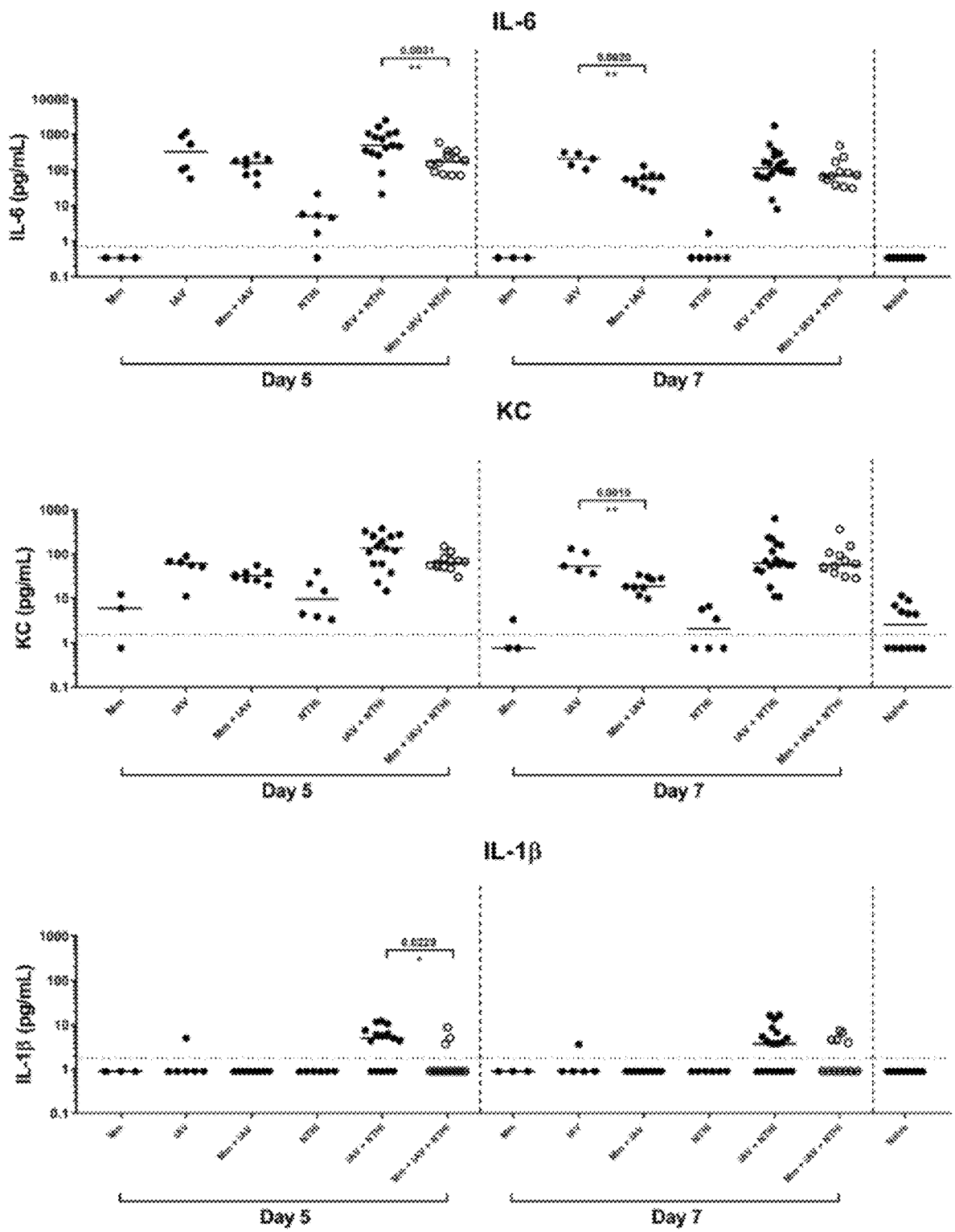

*M. muris* Pre-Treatment Reduces the Nasal Inflammatory Response to IAV and NTHi On day 5, the median titers of inflammatory mediators interleukin-6 (IL-6) and IL-1β were significantly lower in nasal washes from mice in the NTHi otitis media model that were pretreated with *M. muris* (*M. muris*+IAV+NTHi) than from mice with no *M. muris* pretreatment (IAV+NTHi) as follows: IL-6, 171 pg/ml (95% CI, 75.7 to 340) versus 492 pg/ml (95% CI, 304.8 to 1,055), P=0.0031; IL-1β, 0.9 pg/ml (95% CI, 0.895 to 3.73) versus 5.1 pg/ml (95% CI, 0.895 to 7.61), P=0.0229 (FIG. 4A). Keratinocyte chemoattractant (KC) levels were also lower (although not significantly) in nasal washes from the *M. muris*+IAV+NTHi group than from the IAV+NTHi group as follows: 65 pg/ml (95% CI, 51.07 to 83.62) versus 137 pg/ml (95% CI, 60.3 to 255.8), P=0.0725 (FIG. 4A). By day 7, there was no significant difference between median inflammatory mediator titers from the *M. muris*-pretreated (*M. muris*+IAV+NTHi) versus untreated NTHi otitis media group (IAV+NTHi), though titers were higher than those in naive mice or in mice administered *M. muris* or NTHi alone (P<0.05 for IL-6, KC, and IL-1β) (FIG. 4A). IAV administration alone increased the median IL-6 and KC levels in the nasal washes compared with those of the naive, *M. muris* only, or NTHi only treated mice on day 5 and day 7. Interestingly, mice that were pre-treated with *M. muris* prior to IAV challenge (*M. muris*+IAV) had less inflammation in their nares than mice given IAV alone, and this was most pronounced on day 7 for both IL-6 and KC (P=0.0020 and P=0.0010, respectively) (FIG. 4A). Gamma interferon (IFN-γ) and IL-10 were not detected in nasal washes from any treatment.

Example 5

Figure 4B:
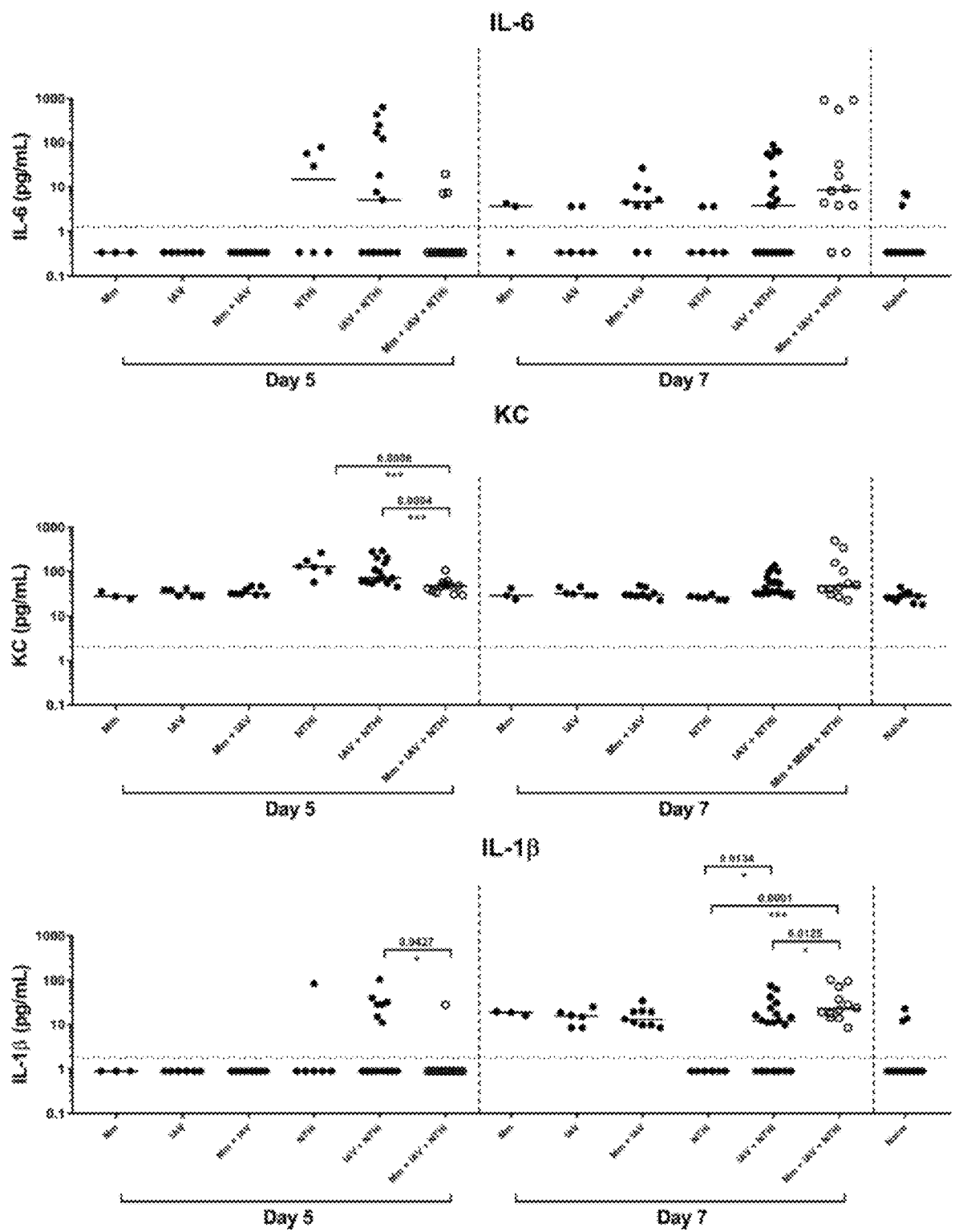

Intranasal Pre-Treatment with *M. muris* Temporarily Reduces Inflammatory Mediator Levels in the Middle Ear Tissue of Mice in the NTHi Otitis Media Model On day 5, IL-6 was elevated in the middle ears of mice receiving NTHi, either alone or in combination with IAV (IAV+NTHi) and *M. muris* (*M. muris*+IAV+NTHi) (FIG. 4B). There was no difference between IL-6 levels in the ears of mice pre-treated with *M. muris* (*M. muris*+IAV+NTHi) compared to untreated mice (IAV+NTHi). KC levels were also elevated in the ears of mice that received NTHi on day 5; however, mice that were pre-treated with *M. muris* (*M. muris*+IAV+NTHi) had significantly reduced KC titers compared with those of mice that received NTHi challenge alone (P=0.0008) or IAV+NTHi challenge (P=0.0004) (FIG. 4B). By day 7, the KC titer returned to baseline value in all of the groups. Pre-treatment of mice with *M. muris* (*M. muris*+IAV+NTHi) prevented the elevated IL-1β response observed in the ears of mice in the NTHi otitis media group (IAV+NTHi) on day 5 (P=0.0427); however, this was reversed by day 7 where mice receiving *M. muris* pre-treatment had higher median IL-1β titers in their ears than untreated mice in the otitis media model (P=0.0125) (FIG. 4B). IFN-γ and IL-10 levels were either very low or not detected in the middle ear tissue, with no difference between median titers for any groups.

Example 6

Figure 5A:
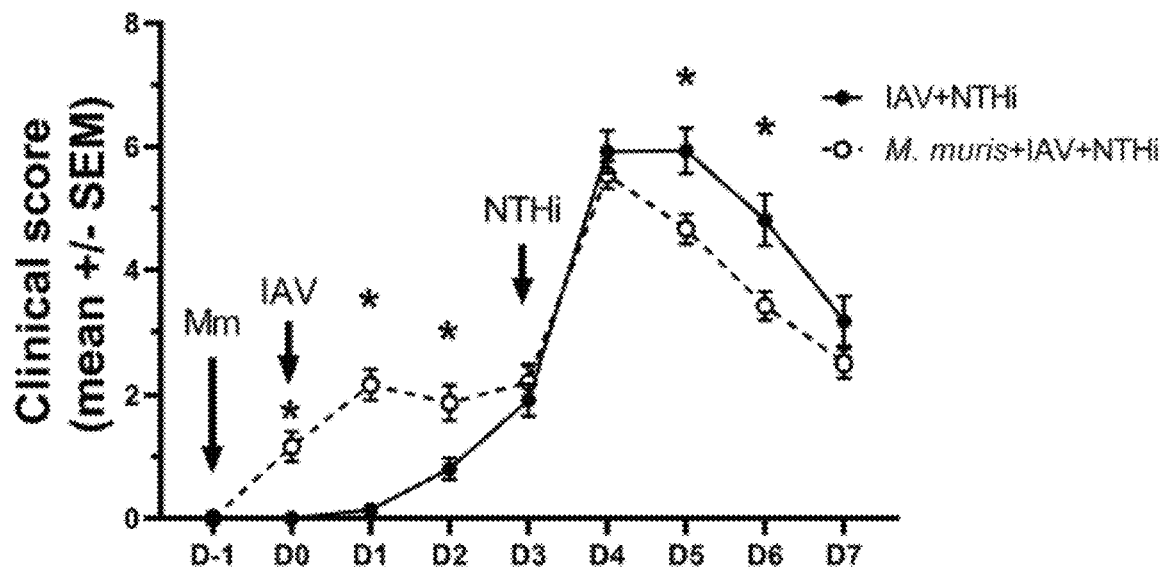
Figure 5B:
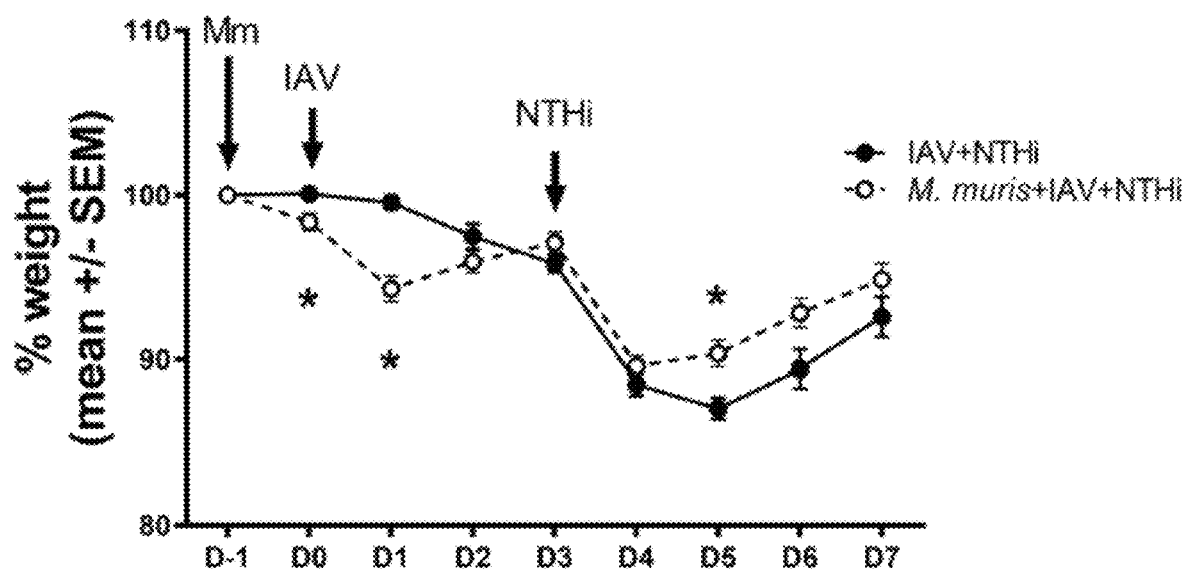

Mice that were Pre-Treated with *M. muris* had Better Clinical Outcomes in the NTHi Otitis Media Model Administration of a single intranasal dose of *M. muris* reduced disease symptoms over the 7-day time frame in the NTHi otitis media model, with lower clinical scores (FIG. 5A) and less weight loss (FIG. 5B) than mice with no *M. muris* pre-treatment (IAV+NTHi). On day 6, the clinical score of mice in the *M. muris*-pre-treated group (*M. muris*+IAV+NTHi) was significantly lower than those that did not receive *M. muris* pre-treatment (IAV+NTHi) (P<0.05) (FIG. 5A). *M. muris* administration alone had no impact on the condition of the mice, with a mean clinical score of 0 to 1 over the 7 days (see FIG. 9 in the supplemental material). *M. muris* only treatment also had no significant impact on weight loss (see FIG. 9). On the day after IAV challenge (day 1), the *M. muris*-treated group (*M. muris*+IAV+NTHi) lost 5% of body weight compared with that of the IAV-treated group (IAV+NTHi) (P<0.01) (FIG. 5B). Similar weight loss also occurred following IAV challenge in the groups that did not receive *M. muris* pre-treatment, but this was observed on day 2 after IAV challenge rather than on day 1 (see FIG. 5B for IAV+NTHi; see also FIG. 9 for IAV only and IAV+NTHi). However, upon NTHi challenge, the mice that were pre-treated with *M. muris* (*M. muris*+IAV+NTHi) had significantly less weight loss than those that had no *M. muris* pre-treatment (IAV+NTHi), and this was sustained from day 5 until day 6 (P<0.01) (FIG. 5B).

Example 7

*M. muris* Challenge Induced a Short-Lived Inflammatory Local Response

Figure 6:
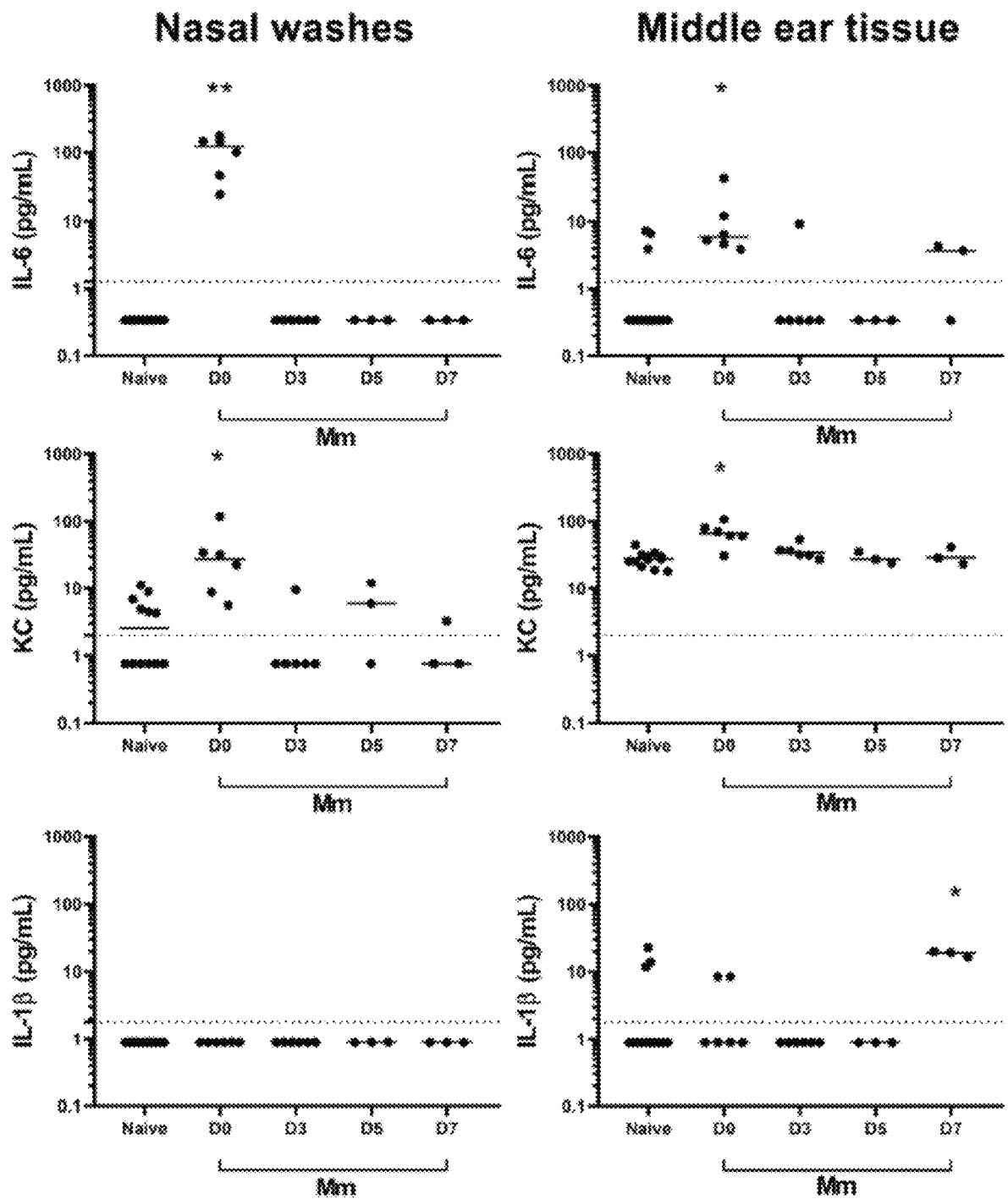

Intranasal challenge with *M. muris* alone induced an inflammatory response in the upper respiratory tract on the day after challenge (day 0, as *M. muris* was administered on day −1), with elevated IL-6 and KC in the nasal washes (P>0.0001 and P=0.0020) and middle ear tissue (P=0.0027 and P=0.0007) compared with those of naive mice (FIG. 6). The IL-6 and KC titers returned to baseline levels by day 3 (4 days after *M. muris* challenge).

Figure 7:
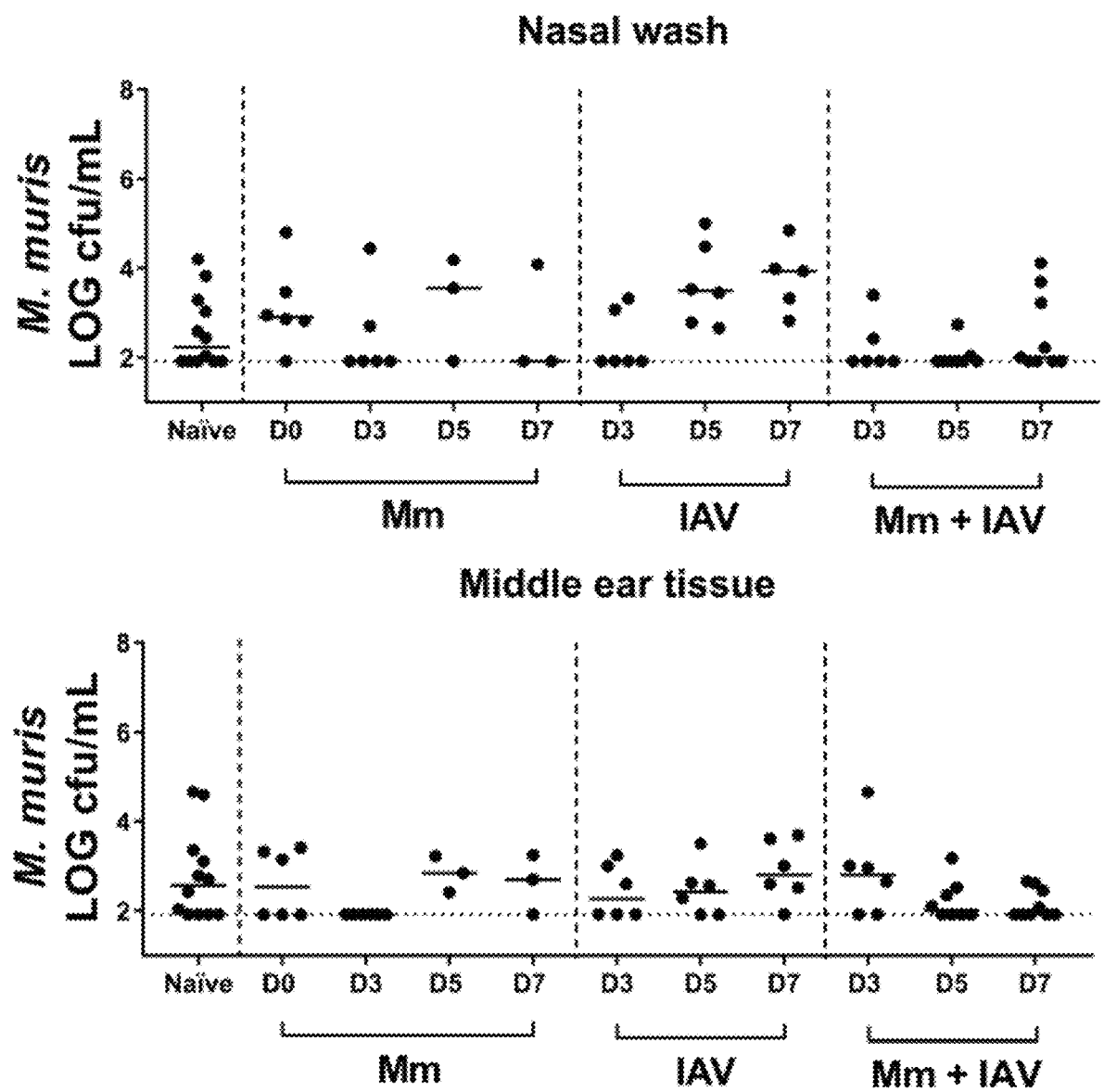

To estimate the duration of *M. muris* colonization following *M. muris* treatment (and whether *M. muris* entered the middle ear), all colonies that appeared *M. muris*-like on nonselective chocolate agar plates were counted in nasal washes and middle ear tissue (FIG. 7). It is important to note that asymptomatic colonization with *M. muris* as part of the normal microbiome was present, as indicated by the *M. muris*-like counts in specimens collected from naive mice (FIG. 7). While the median *M. muris*-like counts were higher (but not significantly so) in *M. muris*-treated mice (*M. muris* only group on day 0 and day 5) than in naive mice, *M. muris* counts also increased when mice were given IAV only, indicating that viral infection amplifies the number of resident *M. muris*-like bacteria in the respiratory tract (FIG. 7). *M. muris* challenge did not increase the number of *M. muris*-like colonies recovered from the middle ear, with similar viability counts in middle ear tissue from challenged and naive mice. Viable counts of *M. muris* were not conducted for specimens from mice treated with both *M. muris* and NTHi (*M. muris*+IAV+NTHi), as these species are indistinguishable on nonselective agar plates.

Example 8

Intranasal Challenge with *H. haemolyticus* Elicited the Same Local Inflammatory Response as *M. Muris*

Intranasal challenge of mice with 5×10⁷ CFU of *H. haemolyticus* (Hh) strains H12 and H19 was conducted and inflammatory responses measured in nasal washes on days 1 and 3 post-challenge. Both strains of *H. haemolyticus* were found to elicit the same local immune profile in mice as *M. muris* (Mm) (FIG. 8). The high IL-6 and KC titres on day 1 post-challenge with either Hh or Mm, which return to baseline by day 3, are indicative of an innate immune stimulation event that may play a role in protection from subsequent exposure to respiratory pathogens.

In summary, intranasal treatment with the commensal Pasteurellaceae species *M. muris* reduces IAV titres in the lung, and reduces NTHi colonization and prevents development of NTHi otitis media in vivo. Intranasal treatment with the commensal Pasteurellaceae species such as *M. muris*. The data suggests that *H. haemolyticus* behaves in the same way as *M. muris*.

REFERENCES

1. Baer, A. and Kehn-Hall, K. (2014) "Viral concentration determination through plaque assays: using traditional and novel overlay systems" *J Vis Exp* 2014:e52065.
2. Christensen, H. and Bisgaard, M. (2018) "Classification of genera of Pasteurellaceae using conserved predicted protein sequences" *Int J Syst Evol Microbiol* 2018; 68:2692-2696
3. Dasaraju, P. V. and Liu. C. "Chapter 93: Infections of the Respiratory System" Medical Microbiology. 4th edition.

Published 1996. Accessed on 28 May 2020: https://www.ncbi.nlm.nih.gov/books/NBK8142/
4. de Vries S P, Burghout P, Langereis J D, Zomer A, Hermans P W, Bootsma H J. (2013) "Genetic requirements for *Moraxella catarrhalis* growth under iron-limiting conditions" *Mol Microbiol* 87:14-29. doi:10.1111/mmi.12081.
5. Herriott R M, Meyer E M, Vogt M. (1970) "Defined nongrowth media for stage II development of competence in *Haemophilus influenzae*" J Bacteriol 101:517-524. doi:10.1128/JB.101.2.517-524.1970
6. Kirkham L A, Corscadden K J, Wiertsema S P, Currie A J, Richmond P C. (2013) "A practical method for preparation of pneumococcal and nontypeable *Haemophilus influenzae* inocula that preserves viability and immunostimulatory activity" *BMC Res Notes* 6:522. doi:10.1186/1756-0500-6-522.
7. Kirkham, L. A. S, Wiertsema, S. P., Mowe, E. A., Bowman, J. M., Riley, T. V., and Richmond, P. C. (2010) "*J Clin Microbiol.* 2010 July; 48(7): 2557-2559.
8. Langereis, J. D., 1, Stol, K., Schweda, E. K., Twelkmeyer, B., Bootsma, H. J., de Vries, S. P. W., Burghout, P., Diavatopoulos, D. A., and Hermans, P. W. M (2012) "Modified Lipooligosaccharide Structure Protects Nontypeable *Haemophilus Influenzae* From IgM-mediated Complement Killing in Experimental Otitis Media" *mBio* 2012 Jul. 3;3(4):e00079-12. doi: 10.1128/mBio.00079-12. Print 2012.
9. Martin B, Prudhomme M, Alloing G, Granadel C, Claverys J P. (2000) "Cross-regulation of competence pheromone production and export in the early control of transformation in *Streptococcus pneumoniae*" *Mol Microbiol* 38:867-878. doi:10.1046/j.1365-2958.2000.02187.x.
10. Pickering J L, Prosser A, Corscadden K J, de Gier C, Richmond P C, Zhang G, Thornton R B, Kirkham L A. (2016) "*Haemophilus haemolyticus* interaction with host cells is different to nontypeable *Haemophilus influenzae* and prevents NTHi association with epithelial cells" *Front Cell Infect Microbiol* 6:50. doi:10.3389/fcimb.2016.00050
11. Price, E. P., Sarovich, D. S., Nosworthy, E., Beissbarth, J., Marsh, R. L., Pickering, J., Kirkham, L. A. S., Keil, A. D., Chang, A. B., Smith-Vaughan, H. C. (2015) "*Haemophilus Influenzae*: Using Comparative Genomics to Accurately Identify a Highly Recombinogenic Human Pathogen" *BMC Genomics* 2015 Aug. 27;16(1):641. doi: 10.1186/s12864-015-1857-x.
12. Reed, K. D. (2015) "Chapter 84—Respiratory Tract Infections: A Clinical Approach" Molecular Medical Microbiology (Second Edition), Volume 3, 2015, Pages 1499-1506
13. Scott N M, Lauzon-Joset J F, Jones A C, Mincham K T, Troy N M, Leffler J, Serralha M, Prescott S L, Robertson S A, Pasquali C, Bosco A, Holt P G, Strickland D H (2017) "Protection against maternal infection-associated fetal growth restriction: proof-of-concept with a microbial-derived immunomodulator" *Mucosal Immunol* 10:789-801. doi:10.1038/mi.2016.85
14. Wiertsema S P, Kirkham L A, Corscadden K J, Mowe E N, Bowman J M, Jacoby P, Francis R, Vijayasekaran S, Coates H L, Riley T V, Richmond P. (2011) "Predominance of nontypeable *Haemophilus influenzae* in children with otitis media following introduction of a 3+0 pneumococcal conjugate vaccine schedule" *Vaccine* 29:5163-5170. doi:10.1016/j.vaccine.2011.05.035.
15. Williams B J, Morlin G, Valentine N, Smith A L. (2001) "Serum resistance in an invasive, nontypeable *Haemophilus influenzae* strain" *Infect Immun* 69:695-705. doi: 10.1128/IAI.69.2.695-705.2001
16. Zoorob, R., Sidani, M. A., Fremont, R. D., and Kihlberg, C., (2012) "Antibiotic Use in Acute Upper Respiratory Tract Infections" *Am Fam Physician*. November 1;86(9): 817-822.

---

The invention claimed is:

1. A method for treating or preventing a viral respiratory infection, a viral and bacterial respiratory co-infection, or a virally induced bacterial respiratory infection in a subject, the method comprising administering to the respiratory tract of the subject an effective amount of one or more bacteria selected from *Haemophilus haemolyticus* and *Muribacter muris*.

2. The method of claim 1, wherein the one or more bacteria is *Haemophilus haemolyticus*.

3. The method of claim 1, wherein the one or more bacteria is *Muribacter muris*.

4. The method of claim 1, wherein the one or more bacteria comprises a combination of two species of bacteria.

5. The method of claim 1, wherein the one or more bacteria comprises a single species of bacteria.

6. The method of claim 1, wherein the one or more bacteria is administered to the subject prior to the subject having a viral and/or bacterial respiratory infection.

7. The method of claim 1, wherein the one or more bacteria is administered to the subject when the subject is infected with a viral and/or bacterial respiratory infection.

8. The method of claim 1, wherein the virus is influenza virus.

9. The method of claim 8, wherein the influenza virus is influenza A virus.

10. The method of claim 1, wherein the viral respiratory infection is caused by influenza virus.

11. The method of claim 1, wherein the bacterial respiratory infection is a *Haemophilus influenzae* infection.

12. The method of claim 11, wherein the *Haemophilus influenzae* is nontypeable *Haemophilus influenzae* (NTHi).

13. A method of reducing viral and/or bacterial titre in the respiratory tract of a subject suffering from a viral respiratory infection, a viral and bacterial respiratory co-infection, or a virally induced bacterial respiratory infection, the method comprising administering to the respiratory tract of the subject an effective amount of one or more bacteria selected from *Haemophilus haemolyticus* and *Muribacter muris*.

14. The method of claim 13, wherein the bacterial respiratory infection is a *Haemophilus influenzae* infection.

15. The method of claim 14, wherein the *Haemophilus influenzae* is nontypeable *Haemophilus influenzae* (NTHi).

16. A method of reducing viral and/or bacterial titre in the respiratory tract of a subject suffering from a viral respiratory infection, a viral and bacterial respiratory co-infection, or a virally induced bacterial respiratory infection, the method comprising administering to the respiratory tract of the subject a pharmaceutical composition comprising one or more bacteria selected from *Haemophilus haemolyticus* and *Muribacter muris*.

17. The method of claim 16, wherein the bacterial respiratory infection is a *Haemophilus influenzae* infection.

18. The method of claim 17, wherein the *Haemophilus influenzae* is nontypeable *Haemophilus influenzae* (NTHi).

19. A method for treating or preventing otitis media in a subject, the method comprising administering to the respiratory tract of the subject an effective amount of one or more bacteria selected from *Haemophilus haemolyticus* and *Muribacter muris*.

* * * * *